(12) United States Patent
Nagamitsu et al.

(10) Patent No.: US 7,839,055 B2
(45) Date of Patent: Nov. 23, 2010

(54) FLAT-PLATE LAMINATION-TYPE CONDUCTIVE POLYMER ACTUATOR AND FLAT-PLATE LAMINATION-TYPE CONDUCTIVE POLYMER ACTUATOR DEVICE AS WELL AS OPERATING METHOD THEREOF

(75) Inventors: Sachio Nagamitsu, Kyoto (JP); Kazuo Yokoyama, Osaka (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/640,093

(22) Filed: Dec. 17, 2009

(65) Prior Publication Data

US 2010/0096950 A1    Apr. 22, 2010

Related U.S. Application Data

(63) Continuation of application No. PCT/JP2009/001293, filed on Mar. 24, 2009.

(30) Foreign Application Priority Data

Mar. 27, 2008    (JP) .............................. 2008-082925

(51) Int. Cl.
    *H01L 41/08* (2006.01)
(52) U.S. Cl. ...................................... 310/328; 310/800
(58) Field of Classification Search ................ 310/330, 310/328, 800
    See application file for complete search history.

(56) References Cited

U.S. PATENT DOCUMENTS

| | | | |
|---|---|---|---|
| 5,977,685 A * | 11/1999 | Kurita et al. ................. | 310/800 |
| 7,259,503 B2 * | 8/2007 | Pei et al. ...................... | 310/800 |
| 7,443,087 B2 * | 10/2008 | Hattori et al. ................ | 310/800 |
| 2005/0218679 A1 | 10/2005 | Yokoyama et al. | |
| 2006/0219983 A1 | 10/2006 | Asai et al. | |
| 2008/0169729 A1 | 7/2008 | Asai | |
| 2010/0039690 A1 * | 2/2010 | Agrawal et al. .............. | 310/300 |

FOREIGN PATENT DOCUMENTS

| | | |
|---|---|---|
| JP | 03-243174 | 10/1991 |
| JP | 06-003630 | 1/1994 |
| JP | 63-289975 | 11/1998 |
| JP | 10-337061 | 12/1998 |
| JP | 11-093827 | 4/1999 |
| JP | 11-169393 | 6/1999 |
| JP | 3723818 | 12/2005 |
| JP | 2006-125396 | 5/2006 |
| JP | 3817259 | 9/2006 |
| JP | 2007-28749 | 2/2007 |
| WO | 2007/007616 | 1/2007 |
| WO | 2007/023625 | 3/2007 |

OTHER PUBLICATIONS

International Search Report issued Jun. 23, 2009 in parent International (PCT) Application No. PCT/JP2009/001293.

* cited by examiner

*Primary Examiner*—J. SanMartin
(74) *Attorney, Agent, or Firm*—Wenderoth, Lind & Ponack, LLP.

(57) ABSTRACT

Conductive polymer films are respectively connected to fixed frames via a link member, and an electrolyte holding layer is placed so as to be made in contact with the conductive polymer films. The fixed frames are regulated by the link member.

14 Claims, 33 Drawing Sheets

| OUTER DIAMETER (Dia.) = | 30mm | 30mm |
| FOCAL LENGTH = | −50mm | 50mm |
| RADIUS OF CURVATURE = | −25.84mm | −25.84mm |

FLAT-PLATE LAMINATION-TYPE CONDUCTIVE POLYMER ACTUATOR AND FLAT-PLATE LAMINATION-TYPE CONDUCTIVE POLYMER ACTUATOR DEVICE AS WELL AS OPERATING METHOD THEREOF

This is a continuation application of International Application No. PCT/JP2009/001293, filed Mar. 24, 2009.

BACKGROUND OF THE INVENTION

The present invention relates to a flat-plate lamination-type conductive polymer actuator and a flat-plate lamination-type conductive actuator device, as well as an operating method thereof.

With the social backgrounds like the falling birthrate and the aging proportion, there have been strong demands for machines, such as home-use robots, which are operated near a person or carry out jobs in cooperation with a person. Under these circumstances, from the viewpoints of flexible movements in response to complicated jobs or ensuring safety upon collision with a person, there are high expectations for artificial muscle actuators that have flexible characteristics like muscles of the human. For such artificial muscle actuators, various materials or control systems therefor, such as those using air pressure, have been proposed. In recent years, as one of these, there has been devised an actuator using a conductive polymer material.

As one example of the actuator using the conductive polymer material, there has been proposed an actuator that utilizes a bimorph-type deformation, as shown in FIGS. 16A, 16B, and 16C. As shown in FIG. 16A, this actuator has a structure in which a solid-state electrolyte molded body 151 is sandwiched between polyaniline films 150a and 150b provided as conductive polymer films. By turning a switch 152 on, an electric potential difference, which is set in a power supply 153, is applied between the polyaniline films 150a and 150b, so that, as shown in FIG. 16B, anions are inserted to the first polyaniline film 150b so that the film 150b is expanded, while anions are removed from the second polyaniline film 150a so that the film 150a is contracted; thus, a bimorph-type deformation is generated. In a case where the electric potential difference is reversed, as shown in FIG. 16C, deformation occurs in a direction reversed relative to that of FIG. 16B (see Patent Document 1 or the like).

In this structure, the deformations are generated by a difference in amount of displacement of the two conductive polymer films functioning as electrodes. On the other hand, a structure has been known in which, by forming the electrolyte holding layer as a liquid or gel-state substance, the two electrodes are prevented from giving effects to each other so as to achieve an actuator that exerts expanding and contracting deformations by taking out only the displacement of one of the conductive polymer films. In this case, with respect to the electrode not utilized for the deformation, it is not necessary to use the conductive polymer material, and a metal electrode is mainly used, and further alternatively, a conductive polymer material may be formed on the metal electrode.

Since this conductive polymer actuator can exert a stress corresponding to muscles at a comparatively low voltage in a range of from 1.5 V to 5.0 V, it is expected to be put into practical use as artificial muscles.

An ionic liquid, which is defined as a melted salt at a room temperature, is utilized as the liquid-state or gel-state electrolyte holding layer. The ionic liquid has drawn a public attention as a new functional liquid, and 1-butyl-3-methylimidazolium or bis (trifluoromethylsulfonyl) imide has been known as such a liquid. Since charges of cationic ions and anionic ions are non-localized, Coulomb forces exerted therebetween are small so that it may be maintained as a liquid at a room temperature. This liquid has a low vapor pressure, with hardly any evaporation loss, and is inflammable. Most liquids of this type are superior in heat and oxidation stability, and have a high lubricating performance. By applying this ionic liquid to an insulating sheet or by forming the ionic liquid itself into a gel, the electrolyte holding layer can be formed.

Moreover, it has been proposed that, since the conductive polymer material is formed into a film, the conductive polymer film is prevented from being buckled by being formed into a cylindrical shape so as to have rigidity. As shown in FIG. 17A, by alternately placing two types of conductive polymer films 60a and 60b having expanding and contracting properties in a circumferential direction so as to be coupled to the ends of the inside cylindrical member 61a and the outside cylindrical member 61b so as to intersect with each other; thus, by allowing one of the films to receive the load when the other film is made to expand, it is possible to provide rigidity. FIG. 17B shows one example of the layout of the conductive polymer films 60a and 60b in the circumferential direction. Moreover, as shown in FIG. 17C, a method is proposed in which this cylindrical member is formed by using conductive polymer materials 62a and 62b so as to increase the amount of displacement (see Patent Document 2 or the like).

Moreover, as shown in FIG. 18, in a structure in which conductive polymer films 70a and 70b are laminated so as to cross each other, they are connected to each other by a link mechanism 71 that can interchange one of displacements in the expanding direction to the other displacement in the contracting direction. It is therefore possible to provide an actuator that exerts a driving force in the expanding direction and rigidity in the contracting direction without necessity of applying a preliminary pressure (see Patent Document 3 or the like).

Patent Document 1: Japanese Unexamined Patent Publication No. 11-169393

Patent Document 2: Japanese Unexamined Patent Publication No. 2006-125396

Patent Document 3: Japanese Patent Publication No. 3817259

However, the actuator having the above-mentioned structure has the following issues.

In the method of Patent Document 1, since the bimorph-type deformation is utilized, it becomes difficult to expand the displacement by further laminating a conductive polymer film, or to freely alternate the expansion of a stress. In order to expand the displacement, the length of the conductive polymer film needs to be changed, and in order to expand the stress, the width of the conductive polymer film needs to be expanded; however, it is impossible to laminate a plurality of conductive polymer films. In particular, the structure of Patent Document 1 makes it difficult to achieve lamination.

The method of Patent Document 2 has a structure in which the conductive polymer films are formed into a cylindrical shape so as to have rigidity, with two types of films 60a and 60b having expanding and contracting properties in the circumferential direction of the cylindrical members 61a and 61b being alternately placed in the width direction thereof as shown in FIG. 17A. Thus being greatly different from a structure in which, as shown in FIG. 16A of Patent Document 1, the conductive polymer films are disposed to be made face to face in the thickness direction, this structure has an issue in that effective insertion and removal of ions through the electrolyte holding layer become difficult. Even supposing that not the layout as shown in FIG. 17B but a layout with higher density in the circumferential direction is made, the movements of ions between the adjacent conductive polymer films are lowered in efficiency, in comparison with the structure in which the polymer films are made face to face with each other. Consequently, it becomes difficult to output sufficient stress and displacement as an actuator. Moreover, in a structure shown in FIG. 17C, since there is given no specific description relating to a supporting member corresponding to the cylindrical member, buckling occurs in the conductive polymer films 62a and 62b, thereby failing to function as an actuator.

In the method of Patent Document 3, although, with respect to both of expansion and contraction, the driving force in the expanding direction and rigidity in the contracting direction are achieved without the necessity of applying a preliminary pressure, there are disadvantages in that the directions in which the driving force can be taken out are dispersed into two directions perpendicularly intersecting with each other, and in that the displacement is not increased even when the number of sheets of the conductive polymer films 70a and 70b to be laminated is increased.

It is therefore an object of the present invention to solve these issues and also to provide a flat-plate lamination-type conductive polymer actuator as well as a flat-plate lamination-type conductive polymer actuator device and an operating method thereof that exert rigidity and a driving force bidirectionally in a contracting direction and in an expanding direction and can expand displacement by lamination.

SUMMARY OF THE INVENTION

In order to solve the above-mentioned problems, the present invention has the following arrangements.

According to a first aspect of the present invention, there is provided a flat-plate lamination-type conductive polymer actuator comprising:

a first link member for holding ends on one side being made face to face with each other of a first conductive polymer film and a second conductive polymer film;

a first fixed frame for holding ends on another side of the first conductive polymer film and the second conductive polymer film;

a second link member for holding ends on one side being made face to face with each other of a third conductive polymer film and a fourth conductive polymer film;

a second fixed frame for holding ends on another side of the third conductive polymer film and the fourth conductive polymer film;

a first electrolyte holding layer disposed between the first conductive polymer film and the third conductive polymer film; and a second electrolyte holding layer disposed between the second conductive polymer film and the fourth conductive polymer film, the first fixed frame and the second fixed frame being placed adjacent to each other, so that the first conductive polymer film and the third conductive polymer film are connected to each other, with the first electrolyte holding layer being interposed therebetween, while the second conductive polymer film and the fourth conductive polymer film are connected to each other, with the second electrolyte holding layer being interposed therebetween, with the first link member being connected to the second link member, wherein by applying an electric potential difference between the first conductive polymer film and the third conductive polymer film, one of the first conductive polymer film and the third conductive polymer film is expanded by a redox reaction, while another thereof is contracted, and by applying an electric potential difference between the second conductive polymer film and the fourth conductive polymer film, one of the second conductive polymer film and the fourth conductive polymer film is contracted by a redox reaction, while another thereof is expanded, and a sum of a contraction displacement in the first fixed frame and a contraction displacement in the second fixed frame is allowed to form a relative displacement between the first fixed frame and the second fixed frame, by connecting the first link member and the second link member.

Therefore, the present invention relates to a flat-plate lamination-type conductive polymer actuator that can exert rigidity and a driving force bidirectionally in the contracting direction and in the expanding direction, and can expand displacement by lamination, and the present invention makes it possible to provide an actuator that can efficiently move ions by using a structure in which contracting and expanding conductive polymer films are made face to face with each other with an electrolyte holding layer interposed therebetween, and that can also efficiently carry out a driving operation while saving energy and space.

BRIEF DESCRIPTION OF THE DRAWINGS

These and other aspects and features of the present invention will become clear from the following description taken in conjunction with the preferred embodiments thereof with reference to the accompanying drawings, in which:

FIG. 16B is a schematic cross-sectional view showing the conventional actuator that utilizes the bimorph-type deformation of FIG. 16A with a switch thereof turned on;

DETAILED DESCRIPTION OF THE PREFERRED EMBODIMENTS

Figure 1A:
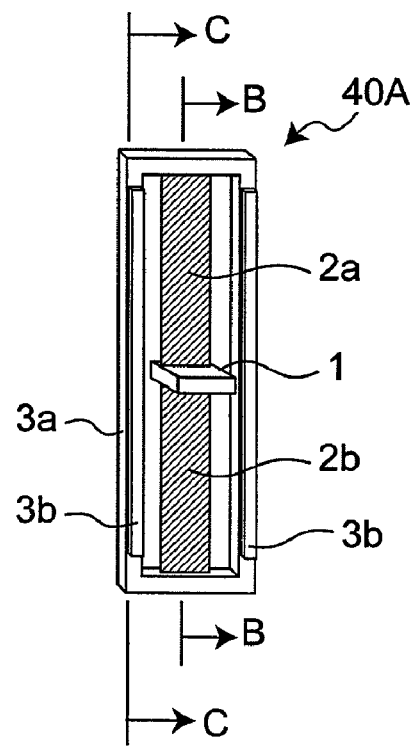
FIG. 1A is a perspective view showing an outer appearance of an actuator unit that forms about a half of a flat-plate lamination-type conductive polymer actuator in accordance with a first embodiment of the present invention.

Before the description of the present invention proceeds, it is to be noted that like parts are designated by like reference numerals throughout the accompanying drawings.

Prior to the detailed description of embodiments of the present invention based upon the drawings, various aspects of the present invention will be explained.

According to a first aspect of the present invention, there is provided a flat-plate lamination-type conductive polymer actuator comprising:

a first link member for holding ends on one side being made face to face with each other of a first conductive polymer film and a second conductive polymer film;

a first fixed frame for holding ends on another side of the first conductive polymer film and the second conductive polymer film;

a second link member for holding ends on one side being made face to face with each other of a third conductive polymer film and a fourth conductive polymer film;

a second fixed frame for holding ends on another side of the third conductive polymer film and the fourth conductive polymer film;

a first electrolyte holding layer disposed between the first conductive polymer film and the third conductive polymer film; and a second electrolyte holding layer disposed between the second conductive polymer film and the fourth conductive polymer film, the first fixed frame and the second fixed frame being placed adjacent to each other, so that the first conductive polymer film and the third conductive polymer film are connected to each other, with the first electrolyte holding layer being interposed therebetween, while the second conductive polymer film and the fourth conductive polymer film are connected to each other, with the second electrolyte holding layer being interposed therebetween, with the first link member being connected to the second link member, wherein by applying an electric potential difference between the first conductive polymer film and the third conductive polymer film, one of the first conductive polymer film and the third conductive polymer film is expanded by a redox reaction, while another thereof is contracted, and by applying an electric potential difference between the second conductive polymer film and the fourth conductive polymer film, one of the second conductive polymer film and the fourth conductive polymer film is contracted by a redox reaction, while another thereof is expanded, and a sum of a contraction displacement in the first fixed frame and a contraction displacement in the second fixed frame is allowed to form a relative displacement between the first fixed frame and the second fixed frame, by connecting the first link member and the second link member.

In accordance with this arrangement, by using the structure which exerts rigidity and a driving force bidirectionally, that is, in the contracting direction and the expanding direction and in which conductive polymer films, which can contract and expand with the electrolyte holding layer interposed therebetween, are made face to face with each other, it becomes possible to obtain a flat-plate lamination-type conductive polymer actuator that can efficiently carry out a driving operation while saving energy and space.

According to a second aspect of the present invention, there is provided the flat-plate lamination-type conductive polymer actuator according to the first aspect, wherein the first link member holds the respective ends of the first and second conductive polymer films and also electrically insulates the respective ends from each other, while the second link member holds the respective ends of the third and fourth conductive polymer films and also electrically insulates the respective ends from each other.

In accordance with this arrangement, by using the structure which can apply an appropriate voltage to each of the conductive polymer films, and appropriately control a stress or an amount of displacement, and can also exert rigidity and a driving force bidirectionally, that is, in the contracting direction and the expanding direction, and in which conductive polymer films, which can contract and expand, are made face to face with each other with an electrolyte holding layer interposed therebetween, it becomes possible to obtain a flat-plate lamination-type conductive polymer actuator that can efficiently carry out a driving operation while saving energy and space.

According to a third aspect of the present invention, there is provided the flat-plate lamination-type conductive polymer actuator according to the first or second aspect, wherein the electric potential difference to be applied between the first conductive polymer film and the third conductive polymer film and the electric potential difference to be applied between the second conductive polymer film and the fourth conductive polymer film are applied so as to make the displacement due to expansion and contraction of the first to fourth conductive polymer films caused by the redox reactions equal to one another.

With this arrangement, it becomes possible to obtain a flat-plate lamination-type conductive polymer actuator that can control a stress or an amount of displacement appropriately, with rigidity as the actuator being maintained, by applying an appropriate voltage to each of the conductive polymer films.

According to a fourth aspect of the present invention, there is provided the flat-plate lamination-type conductive polymer actuator according to the third aspect, wherein the first and second conductive polymer films are made by a same material so as to have a same length, and the third and fourth conductive polymer films are made by a same material so as to have a same length.

With this arrangement, it becomes possible to obtain a flat-plate lamination-type conductive polymer actuator that can make the voltage to be applied to the conductive polymer films substantially constant, and also simplify the controlling operations of a stress or an amount of displacement, with rigidity as the actuator being maintained.

According to a fifth aspect of the present invention, there is provided a flat-plate lamination-type conductive polymer actuator device comprising:

a plurality of flat-plate lamination-type conductive polymer actuators according to the first or second aspect, the actuators being connected with one another with the electrolyte holding layer being interposed therebetween, wherein by applying an electric potential difference between the conductive polymer films, one of the adjacent conductive polymer films is expanded by a redox reaction, with another thereof being contracted thereby.

In accordance with this arrangement, it becomes possible to obtain a flat-plate lamination-type conductive polymer actuator that can exert rigidity and a driving force bidirectionally, that is, in the contracting direction and the expanding direction, and expand the displacement or the stress by laminating layers with a high density, and also efficiently carry out a driving operation while saving energy and space, by using a structure in which conductive polymer films, which can contract and expand, are made face to face with each other with an electrolyte holding layer interposed therebetween.

According to a sixth aspect of the present invention, there is provided the flat-plate lamination-type conductive polymer actuator device comprising:

a plurality of flat-plate lamination-type conductive polymer actuators according to the first or second aspect, the actuators being connected with one another with the electrolyte holding layer being interposed therebetween, wherein by applying an electric potential difference between the conductive polymer films, one of the adjacent conductive polymer films is expanded by a redox reaction, with another thereof being contracted thereby, wherein, upon connecting the plurality of flat-plate lamination-type conductive polymer actuators to one another, the fixed frames are coupled to one another.

In accordance with this arrangement, it becomes possible to obtain a flat-plate lamination-type conductive polymer actuator that can expand the displacement by laminating layers with a high density, and also efficiently carry out a driving operation while saving energy and space, by using a structure in which conductive polymer films, which can contract and expand, are made face to face with each other with an electrolyte holding layer interposed therebetween.

According to a seventh aspect of the present invention, there is provided the flat-plate lamination-type conductive polymer actuator device comprising:

a plurality of flat-plate lamination-type conductive polymer actuators according to the first or second aspect, the actuators being connected with one another with the electrolyte holding layer being interposed therebetween, wherein by applying an electric potential difference between the conductive polymer films, one of the adjacent conductive polymer films is expanded by a redox reaction, with another thereof being contracted thereby, wherein, upon connecting the plurality of flat-plate lamination-type conductive polymer actuators to one another, the link members are coupled to one another.

In accordance with this arrangement, it becomes possible to obtain a flat-plate lamination-type conductive polymer actuator that can expand the stress by laminating layers with a high density, and also efficiently carry out a driving operation while saving energy and space, by using a structure in which conductive polymer films, which can contract and expand, are made face to face with each other with an electrolyte holding layer interposed therebetween.

According to an eighth aspect of the present invention, there is provided the flat-plate lamination-type conductive polymer actuator device comprising:

a plurality of flat-plate lamination-type conductive polymer actuators according to the first or second aspect, the actuators being connected with one another with the electrolyte holding layer being interposed therebetween, wherein by applying an electric potential difference between the conductive polymer films, one of the adjacent conductive polymer films is expanded by a redox reaction, with another thereof being contracted thereby, wherein, upon connecting at least three flat-plate lamination-type conductive polymer actuators to one another, the conductive polymer films placed on every other fixed frame are linearly coupled to one another so as to be charged.

In accordance with this arrangement, with respect to wiring that becomes more complicated by laminating layers, it is possible to obtain a flat-plate lamination-type polymer actuator that can achieve simplified structure and manufacturing processes by using a substantially directly formed wiring, without depending on the displacement at the time of driving.

According to a ninth aspect of the present invention, there is provided the flat-plate lamination-type conductive polymer actuator according to the first or second aspect, wherein the first and fourth conductive polymer films are made by a sheet of conductive polymer film, the third and second conductive polymer films are made by another sheet of conductive polymer film, and the first link member and the second link member are integrally connected to each other to form a single insulating link member so that the sheet of conductive polymer film and the other sheet of conductive polymer film are held by the insulating link member so as not to be made in contact with each other, so as to intersect with each other in center portions.

In accordance with this arrangement, it is possible to obtain a flat-plate lamination-type polymer actuator having a structure in which an insulating performance between conductive polymer films having different polarities in applied voltages can be improved, simplified wiring is achieved by integrally forming conductive polymer films having the same polarity in applied voltages, and it becomes possible to avoid problems such as disconnection and the like of the conductive polymer films by avoiding a concentrated stress at bent portions of link members at the time of their connecting process.

According to a 10th aspect of the present invention, there is provided the flat-plate lamination-type conductive polymer actuator device according to the first or second aspect, wherein the first link member and the second link member are formed by the same members or different members that are coupled to each other.

According to an 11th aspect of the present invention, there is provided the flat-plate lamination-type conductive polymer actuator device comprising:

a plurality of flat-plate lamination-type conductive polymer actuators according to the first or second aspect, the actuators being connected with one another with the electrolyte holding layer being interposed therebetween, wherein by applying an electric potential difference between the conductive polymer films, one of the adjacent conductive polymer films is expanded by a redox reaction, with another thereof being contracted thereby, wherein, upon connecting the plurality of conductive polymer actuators to one another, a spacer is interposed between the fixed frames of the adjacent conductive polymer actuators.

With this arrangement, it becomes possible to allow the above-mentioned fixed frames to smoothly slide on each other by using the spacer.

According to a 12th aspect of the present invention, there is provided a robot hand comprising: the flat-plate lamination-type conductive polymer actuator device according to the fifth aspect, being disposed therein as a driving source for fingers so as to be capable of bending.

According to a 13th aspect of the present invention, there is provided a pair of glasses comprising: the flat-plate lamination-type conductive polymer actuator device according to the fifth aspect used for moving a movable lens relative to a lens frame.

According to a 14th aspect of the present invention, there is provided an operating method for a flat-plate lamination-type conductive polymer actuator, the conductive polymer actuator comprising:

a first link member for holding ends on one side being made face to face with each other of a first conductive polymer film and a second conductive polymer film, a first fixed frame for holding ends on another side of the first conductive polymer film and the second conductive polymer film, a second link member for holding ends on one side being made face to face with each other of a third conductive polymer film and a fourth conductive polymer film, a second fixed frame for holding ends on another side of the third conductive polymer film and the fourth conductive polymer film, a first electrolyte holding layer disposed between the first conductive polymer film and the third conductive polymer film, and a second electrolyte holding layer disposed between the second conductive polymer film and the fourth conductive polymer film;

the first fixed frame and the second fixed frame being placed adjacent to each other so that the first conductive polymer film and the third conductive polymer film are connected to each other, with the first electrolyte holding layer being interposed therebetween, while the second conductive polymer film and the fourth conductive polymer film are connected to each other, with the second electrolyte holding layer being interposed therebetween, with the first link member being connected to the second link member, the method comprising:

by applying an electric potential difference between the first conductive polymer film and the third conductive polymer film, expanding one of the first conductive polymer film and the third conductive polymer film by a redox reaction, while contracting another thereof; and by applying an electric potential difference between the second conductive polymer film and the fourth conductive polymer film, contracting one of the second conductive polymer film and the fourth conductive polymer film by a redox reaction, while expanding another thereof, wherein a sum of a contraction displacement in the first fixed frame and a contraction displacement in the second fixed frame is allowed to form a relative displacement between the first fixed frame and the second fixed frame, by connecting the first link member and the second link member.

Referring to the drawings, the following description will discuss embodiments of the present invention.

First Embodiment

FIGS. 1A to 3C are views showing one example of a flat-plate lamination-type conductive polymer actuator in accordance with a first embodiment of the present invention and an operation method thereof. FIG. 2A is a perspective view showing the entire structure of a flat-plate lamination-type conductive polymer actuator 40 of the first embodiment. The conductive polymer actuator 40 has a structure in which a plurality (two for example) of actuator units, serving as constituent members thereof, are laminated with an electrolyte holding layer 6 (such as a first electrolyte holding layer and a second electrolyte holding layer) being sandwiched therebetween. More specifically, two first actuator units 40A are laminated (another first actuator unit 40A shown in FIG. 1A is referred to as a second actuator unit 40B, as will be described later, and in the figure, the actuator unit 40A and the actuator unit 40B are laminated) with the electrolyte holding layer 6 being sandwiched therebetween, so that the conductive polymer actuator 40 is formed.

Figure 1B:
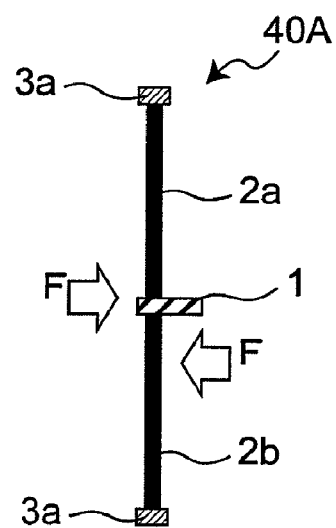
FIG. 1B is a cross-sectional view, taken along line B-B of FIG. 1A, showing about the half of the flat-plate lamination-type conductive polymer actuator of FIG. 1A from a side face thereof.
Figure 1C:
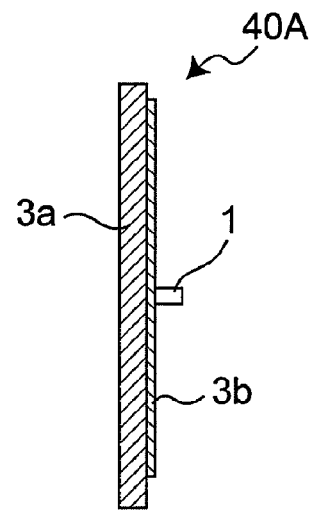
FIG. 1C is a cross-sectional view, taken along line C-C of FIG. 1A, showing about the half of the flat-plate lamination-type conductive polymer actuator of FIG. 1A from the side face thereof.

FIG. 1A is a perspective view showing the first actuator unit 40A. FIG. 1B is a cross-sectional view, taken along line B-B, showing the first actuator unit 40A of FIG. 1A from a side face thereof. FIG. 1C is a cross-sectional view, taken along line C-C, showing the first actuator unit 40A of FIG. 1A from the side face thereof.

In FIG. 1A, reference symbols 2a and 2b represent elastic members made of a conductive polymer, each of which has a rectangular shape such as a rectangle, and is deformed in an expanded or contracted manner in response to a redox reaction, and made of a film-shaped conductive polymer film (such as a first conductive polymer film and a second conductive polymer film). As a conductive polymer forming the respective conductive polymer films 2a and 2b, polypyrrole, polyaniline, or the like may be utilized, in which polypyrrole is preferably used because of a high amount of displacement thereof. Moreover, the thicknesses of the conductive polymer films 2a and 2b are preferably set in a range of from 5 μm to about 30 μm respectively. Although also greatly dependent on the material property, in a case where the thickness of each of the conductive polymer films 2a and 2b is less than 5 μm, the resulting film becomes weak in strength, while, in a case where it is thicker than 30 μm, the generated displacement becomes smaller because of difficulty in allowing ions to reach the inside of the film and to come out therefrom, and an operation rate thereof is lowered simultaneously; consequently, these ranges are not suitably applied. In one actual example of the first embodiment, the conductive polymer films 2a and 2b each having a thickness of 15 μm, a length of 25 mm, and a width of 5 mm are used.

FIG. 1B is a cross-sectional view, taken along line B-B of FIG. 1A, in the longitudinal direction perpendicular to the conductive polymer films 2a and 2b with respect to the first actuator unit 40A of the flat-plate lamination-type conductive polymer actuator 40 shown in FIG. 1A. The conductive polymer films 2a and 2b are electrically connected to each other via an electrically insulating link member (such as first link member) 1 in a rectangular plate shape, and the respective ends are secured and held respectively to the upper and lower ends in FIG. 1A of an insulating fixed frame (such as first fixed frame) 3a having a quadrilateral shape. In this case, as an example, the fixed frame is allowed to have an insulating property; however, not being limited thereto, in a case where the fixed frame is a non-insulating member, an insulating member may be placed between the electrode or the conductive polymer film, particularly the electrolyte holding layer, and the fixed frame. Therefore, as shown in FIGS. 1A and 1B, the conductive polymer films 2a and 2b are held in a tense state by tensions exerted inside the fixed frame 3a. For this reason, the conductive polymer films 2a and 2b are held in a constant state against an external force F applied in the direction perpendicular to the longitudinal direction of the conductive polymer films 2a and 2b (the thickness direction of the conductive polymer films 2a and 2b) without being buckled, due to tensions of the conductive polymer films 2a and 2b. Further, quadrilateral pillar shaped and rod-shaped spacers 3b are provided to surfaces of the side portions of the fixed frame 3a in the longitudinal direction. The spacers 3b are preferably made of Teflon (registered trademark) or the like serving as a material having low frictional resistance and high corrosion resistance. In this manner, by applying such a material having a low frictional resistance as the spacers 3b, the spacers 3b are designed to be easily slid on contact faces of opposing and contacting members. For simplification of production, the spacers 3b are preferably made of an insulating material. In a case of using a non-insulating material as the spacers 3b, an insulating member needs to be placed between the electrode or the conductive polymer film, particularly the electrolyte holding layer, and each of the spacers 3b.

Figure 1D:
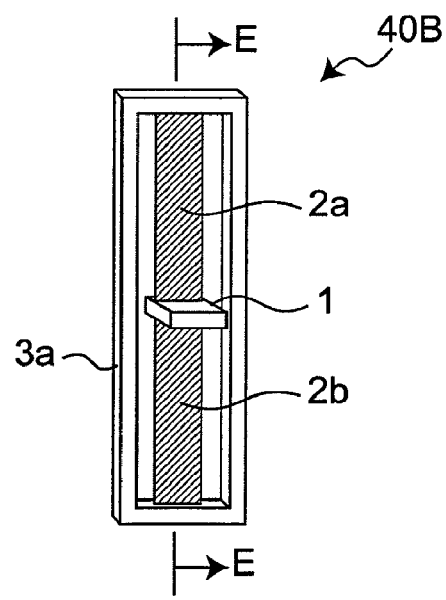
FIG. 1D is a perspective view showing about a half of a flat-plate lamination-type conductive polymer actuator different from the flat-plate lamination-type conductive polymer actuator of FIG. 1A in that no spacers are installed therein.
Figure 1E:
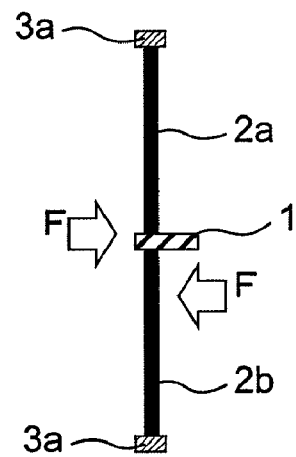
FIG. 1E is a cross-sectional view, taken along line E-E of FIG. 1D, showing about the half of the flat-plate lamination-type conductive polymer actuator of FIG. 1D from a side face thereof.

FIG. 1D is a perspective view showing an actuator unit 40B provided with no spacers 3b, in comparison with the first actuator unit 40A of the flat-plate lamination-type conductive polymer actuator of FIG. 1A. FIG. 1E is a cross-sectional view, taken along line E-E, showing the second actuator unit 40B of FIG. 1D from the side face thereof. The first actuator unit 40A and the second actuator unit 40B have completely the same shape and the same structure except for the spacers 3b.

Basically, upon forming the flat-plate lamination-type conductive polymer actuator 40 according to the first embodiment, two pieces of the first actuator units 40A of FIG. 1A are prepared, and by superposing on the surface side of the first actuator unit 40A of FIG. 1A the surface side of another first actuator unit 40A in FIG. 1A (hereinafter, referred to as a second actuator unit 40B), the spacers 3b are laminated while the spacers 3b are made in slidable contact with each other.

In the following description, in order to separately explain operations of the first actuator unit 40A and the second actuator unit 40B, the following correlations are confirmed. The conductive polymer films 2a and 2b of the second actuator unit 40B are illustrated as conductive polymer films 4b and 4a (such as a third conductive polymer film and a fourth conductive polymer film). The fixed frame 3a is illustrated as a fixed frame (such as the second fixed frame) 5a. The spacers 3b are illustrated as spacers 5b. Since the link member 1 is commonly utilized by the two actuator units, namely, the first actuator unit 40A and the second actuator unit 40B, the link member 1 is illustrated as it is. The link member 1 of FIG. 2A (such as a link member formed by the first link member and the second link member integrally connected with each other) is the same as the link member 1 of FIG. 1A. One of the ends (the end on the rear side in FIG. 2A) is connected to the conductive polymer films 2a and 2b of the first actuator unit 40A, with the other end (the end on the front side in FIG. 2A) being connected to the conductive polymer films 4b and 4a of the second actuator unit 40B. The conductive polymer films 4b and 4a, the fixed frame 5a, and the spacers 5b are simply indicated by the different reference symbols, and the basic structures, materials, or functions thereof are the same as those of the respective members of the first actuator unit 40A.

Figure 2A:
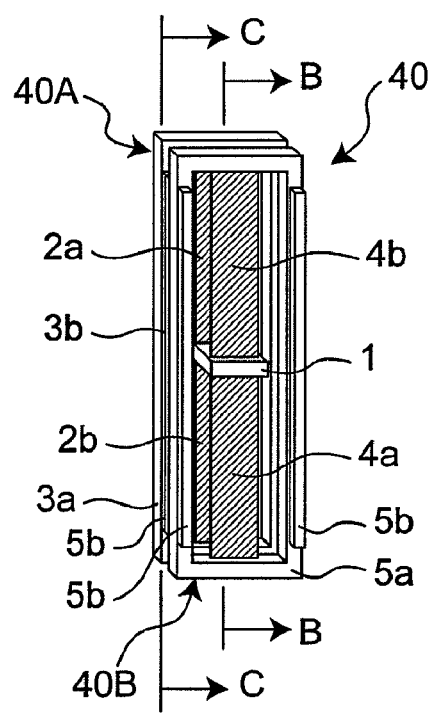
FIG. 2A is a perspective view showing an outer appearance of the flat-plate lamination-type conductive polymer actuator in accordance with the first embodiment of the present invention.
Figure 2B:
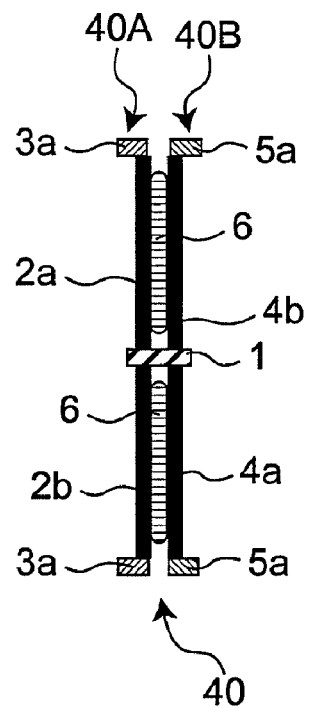
FIG. 2B is a cross-sectional view taken along line B-B of FIG. 2A in a longitudinal direction perpendicular to a conductive polymer film of the flat-plate lamination-type conductive polymer actuator in accordance with the first embodiment of the present invention shown in FIG. 2A.
Figure 2C:
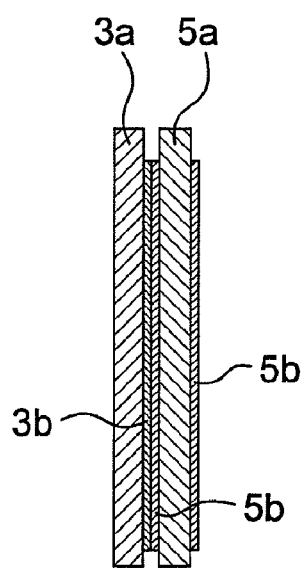
FIG. 2C is a cross-sectional view taken along line C-C of FIG. 2A in the longitudinal direction perpendicular to the conductive polymer film of the flat-plate lamination-type conductive polymer actuator in accordance with the first embodiment of the present invention shown in FIG. 2A.

FIG. 2A is a perspective view showing an outer appearance of the flat-plate lamination-type conductive polymer actuator 40 according to the first embodiment, which is configured by the first actuator unit 40A and the second actuator unit 40B. FIG. 2B is a cross-sectional view taken along line B-B in the longitudinal direction of the conductive polymer films 2a, 2b, 4b, and 4a of the conductive polymer actuator 40. FIG. 2C is a cross-sectional view taken along line C-C in the longitudinal direction of the conductive polymer films 2a, 2b, 4b, and 4a.

In FIG. 2A, the conductive polymer films 4a and 4b are designed to be connected to each other via the link member 1 (such as the second link member) shown in FIG. 1A. Moreover, as shown in FIG. 2B, an electrolyte holding layer 6 formed by a gel-state ionic liquid is disposed so as to be made in contact with the conductive polymer film 2a and the conductive polymer film 4b above the link member 1. Similarly, below the link member 1, an electrolyte holding layer 6 formed by a gel-state ionic liquid is disposed so as to be made in contact with the conductive polymer film 2b and the conductive polymer film 4a. The thicknesses of the respective electrolyte holding layers 6 are preferably set in a range of from 5 μm to 50 μm. With the thickness of the electrolyte holding layer 6 exceeding 5 μm, it is impossible to closely dispose the conductive polymer films. In contrast, with the thickness of the electrolyte holding layer 6 less than 50 μm, the number of ions contained in the electrolyte holding layer 6 is smaller, with a result that a driving force or an amount of displacement is lowered. In this case, since the electrolyte holding layer is in a gel state, it is not joined to none of the conductive polymer films 2a, 4b, 2b, and 4a while being in contact with the electrolyte holding layer 6, thereby being slidable. In one specific example according to the first embodiment, the electrolyte holding layers 6 each having a thickness of 30 μm are used. As shown in FIG. 2C, similarly to the spacers 3b of the fixed frame 3a, quadrilateral pillar shaped and rod-shaped spacers 5b are provided to the two sides of the fixed frame 5a so that the fixed frame 3a and the fixed frame 5a are made apart from each other by the spacer 3b and the spacer 5b, with a gap corresponding to the thickness of the electrolyte holding layer 6 maintained. Specifically, the respective heights of the spacers 3b and 5b are set to about a half of the thickness of the electrolyte holding layer 6.

The spacers 3b secured to the fixed frame 3a and the spacers 5b secured to the fixed frame 5a are made in contact with each other so as to be slidable.

As shown in FIG. 2B, the fixed frame 3a and the fixed frame 5 are restrained by the link member 1. However, this structure is characterized in that they are freely movable in expanding and contracting directions of the conductive polymer films 2a, 4b, 2b, and 4a.

Figure 2D:
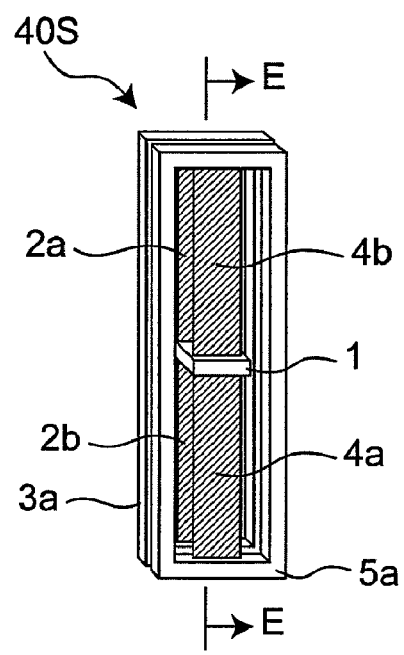
FIG. 2D is a perspective view showing a flat-plate lamination-type conductive polymer actuator different from the flat-plate lamination-type conductive polymer actuator of FIG. 2A in that no spacers are installed therein.
Figure 2E:
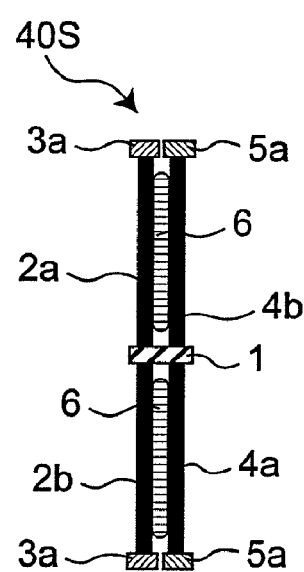
FIG. 2E is a cross-sectional view, taken along line E-E of FIG. 2D, showing the flat-plate lamination-type conductive polymer actuator of FIG. 2D from the side face thereof.

FIG. 2D is a perspective view showing a flat-plate lamination-type conductive polymer actuator 40S provided with no spacers 3b and no spacers 5b in comparison with the flat-plate lamination-type conductive polymer actuator of FIG. 2A. FIG. 2E is a cross-sectional view, taken along line E-E, showing the flat-plate lamination-type conductive polymer actuator 40S of FIG. 2D from the side face thereof. In this structure, since no spacers 3b and 5b are provided, portions each corresponding to the thickness of the electrolyte holding layer 6 are covered by increasing the thicknesses of the fixed frames 3a and 5a so that the fixed frames 3a and 5a are directly made in slidable contact with each other. This arrangement is advantageous in the simple structure thereof. However, it is necessary to form the fixed frames 3a and 5a with a material having a low frictional coefficient. In a case where the fixed frames 3a and 5a are coupled and secured with each other so as not to be slide as will be described later, such a material having a low frictional coefficient like Teflon (registered trademark) tends to be hardly joined to each other with use of a resin adhesive, so that, in some cases, small openings or the like may be required to be formed so as to be joined by bolts. The following description will discuss the structure with no spacers 3b and 5b so as to preferentially obtain the advantage of the simple structure.

Figure 3A:
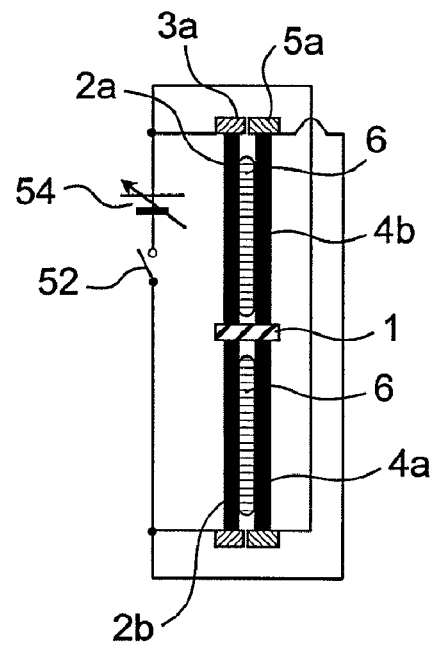
FIG. 3A is a wiring diagram in a zero potential state (initial state) showing one example of the flat-plate lamination-type conductive polymer actuator of the first embodiment of the present invention and applying a voltage to the conductive polymer actuator.
Figure 3B:
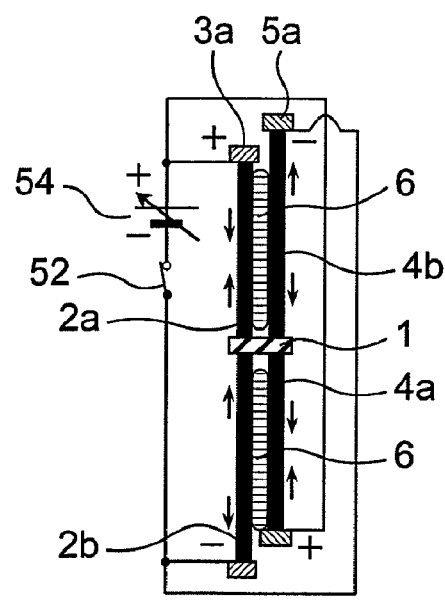
FIG. 3B is a view showing a voltage and a direction of displacement upon turning on a switch to the flat-plate lamination-type conductive polymer actuator of the first embodiment of the present invention shown in FIG. 3A.
Figure 3C:
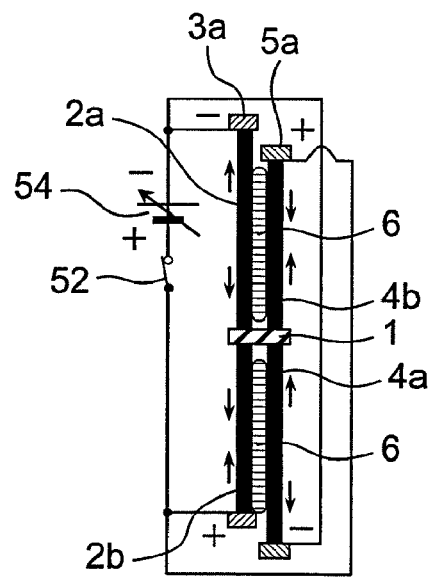
FIG. 3C is a view showing a case of applying a voltage to the flat-plate lamination-type conductive polymer actuator of the first embodiment of the present invention shown in FIG. 3A in a direction reversed relative to that of the voltage shown in FIG. 3B.

FIG. 3A is a wiring diagram showing one example of the flat-plate lamination-type conductive polymer actuator according to the first embodiment of the present invention and application of a voltage to the conductive polymer actuator. FIG. 3B is a view showing a voltage and a direction of displacement upon turning a switch on in the conductive polymer actuator of FIG. 3A. FIG. 3C is a view showing a state where, in the conductive polymer actuator in FIG. 3A, a voltage is applied in a direction reversed relative to the voltage applying direction of FIG. 3B. A power-supply circuit 54 having a built-in voltage control circuit has one of electrodes connected to the conductive polymer films 2b and 4b with the other electrode being connected to the conductive polymer films 2a and 4b via the switch 52. The following description will discuss the driving operations of the conductive polymer films 2a, 4b, 2b, and 4a, as being carried out due to incoming and outgoing cations. As factors allowing the conductive polymer films 2a, 4b, 2b, and 4a to expand and contract, incoming and outgoing anions, incoming and outgoing cations, change in the polymer structure, or the like are considered. In a case of a material such as polypyrrole, the deformation mechanism thereof is regarded to be mainly derived from the incoming and outgoing cations. This mechanism is dependent on the types of the conductive polymer or the ionic liquid to be used.

As shown in FIG. 3B, it becomes possible to drive the link member 1 by expansion and contraction of the conductive polymer films 2a, 4b, 2b, and 4a due to ionic exchange to and from the electrolyte holding layers 6. The conductive polymer films 2a and 2b as well as the conductive polymer films 4b and 4a are designed to alternately carry out expansion and contraction respectively so that, by setting the amounts of displacement to be always equal to each other, the link member 1 is allowed to generate rigidity and a driving force reciprocating in two directions with no necessity of any preliminary pressure application and without being buckled. As the method for setting the amounts of displacement of the conductive polymer films 2a and 2b and the amounts of displacement of the conductive polymer films 4b and 4a to be always equal to each other, the respective potential differences between the conductive polymer films 2a and 2b as well as between the conductive polymer films 4b and 4a are effectively applied thereto such that the displacements of expansion and contraction between the conductive polymer films 2a and 2b as well as between the conductive polymer films 4b and 4a due to redox reactions are made to be equal to each other. Alternatively, the above-mentioned method is effectively carried out by forming the conductive polymer films 2a and 2b as well as the conductive polymer films 4b and 4a into the same length by using the same material so that the absolute values of voltages to be applied respectively between the conductive polymer films 2a and 2b as well as between the conductive polymer films 4b and 4a are made equal to each other. In a case where there is a difference in characteristics or in dimension between the conductive polymer films 2a and 2b as well as between the conductive polymer films 4b and 4a, by optimally controlling the values of voltages or time change thereof to be given respectively between the conductive polymer films 2a and 2b as well as between the conductive polymer films 4b and 4a, it also becomes possible to obtain the same effect.

In FIG. 3B, a minus electric potential is applied across the conductive polymer films 2b and 4b, while a plus electric potential is applied across the conductive polymer films 2a and 4a, from the power-supply circuit 54. In this case, cations are attracted to the conductive polymer films 2b and 4b on the negative electrode side, and are allowed to enter the insides of the conductive polymer films 2b and 4b. During this process, the conductive polymer films 2b and 4b are respectively expanded in the longitudinal direction. In contrast, since the conductive polymer films 2a and 4a are on the positive electrode side, cations inside the conductive polymer films 2a and 4a are allowed to move into the electrolyte holding layer 6 so that the conductive polymer films 2a and 4a are respectively contracted in the longitudinal direction. In this case, similarly to the above-described case of FIG. 1B, the amounts of displacement due to expansion and contraction between the conductive polymer films 2a and 2b as well as between the conductive polymer films 4a and 4b are respectively set to be equal to each other. As a result, the fixed frames 3a and 5 are displaced relatively in the expanding and contracting directions of the conductive polymer films with respect to the link member 1. Supposing that the link member 1 is fixed, in comparison with the initial positions of the fixed frames 3a and 5 of FIG. 3A, the fixed frame 3a is moved downward from the initial position by the amount of displacement of one of the conductive polymer films while the fixed frame 5 is moved upward from the initial position by the amount of displacement of one of the conductive polymer films, in the case of FIG. 3B. Consequently, the amount of relative displacement between the fixed frames 3a and 5 is about two times longer than the amount of displacement of one of the conductive polymer films. The driving force is about one time of the driving force of one of the conductive polymer films, that is, equal thereto. Moreover, this structure is characterized in that rigidity is exerted against an external force in a compression direction by the conductive polymer films 2a and 4a being contracted, as a stress in response to expansion by the fixed frames 3 and 5, as well as in that, against an external force in a stretch direction, rigidity is maintained by the conductive polymer films 4a and 4b being expanded.

In FIG. 3C, in a reverse manner, a positive electric potential is applied to the conductive polymer films 2b and 4b from the power-supply circuit 54, while a negative electric potential is applied to the conductive polymer films 2a and 4a therefrom, with a result that the direction of displacement is reversed relative to that of FIG. 3B. That is, supposing that the link member 1 is fixed, relative to the initial positions of the fixed frames 3a and 5 of FIG. 3A, the fixed frame 3a is moved upward from the initial position by the amount of displacement of one of the conductive polymer films while the fixed frame 5 is moved downward from the initial position by the amount of displacement of one of the conductive polymer films in the case of FIG. 3C. In this case, the amounts of displacement and the driving force as well as rigidity are the same as those of FIG. 3B.

In particular, the flat-plate lamination-type conductive polymer actuator according to the first embodiment is also characterized in that the conductive polymer films 2a and 4b as well as the conductive polymer films 2b and 4a, which are contracted and expanded, are made face to face with each other via the respective electrolyte holding layers 6. In a case where a driving force is generated by further repeating expansion and contraction, it is also said that, between the conductive polymer films 2a and 4b as well as between the conductive polymer films 2b and 4a, which are made face to face with each other, reciprocating movements of ions remaining in the insides of the conductive polymer films 2a and 4b as well as in the insides of the conductive polymer films 2b and 4a are generated similarly to a so-called charge in a capacitor, so that electrical energy consumption from the power-supply circuit 54 can be suppressed to a minimum level. Therefore, this layout in the structure is characterized in that it is possible to save the space and also to provide the best mode capable of carrying out a driving operation efficiently while saving energy.

As described above, in accordance with the first embodiment, there is provided such a structure in which the conductive polymer films 2a and 4b as well as the conductive polymer films 2b and 4a, each of which is expanded and contracted and exerts rigidity and a driving force bidirectionally in the contracting direction and the expanding direction, are made face to face with each other with the electrolyte holding layers 6 respectively interposed therebetween, with a result that there can be provided the flat-plate lamination-type conductive polymer actuator capable of carrying out a driving operation efficiently while saving energy and space.

Second Embodiment

FIGS. 4A to 4E are cross-sectional views showing one example of a flat-plate lamination-type conductive polymer actuator device 41 in accordance with a second embodiment of the present invention. Those portions of the same functions as those of the first embodiment are indicated by the same reference symbols, and overlapped description will not be repeated. Moreover, description on the case of FIG. 4F will be given later.

Figure 4A:
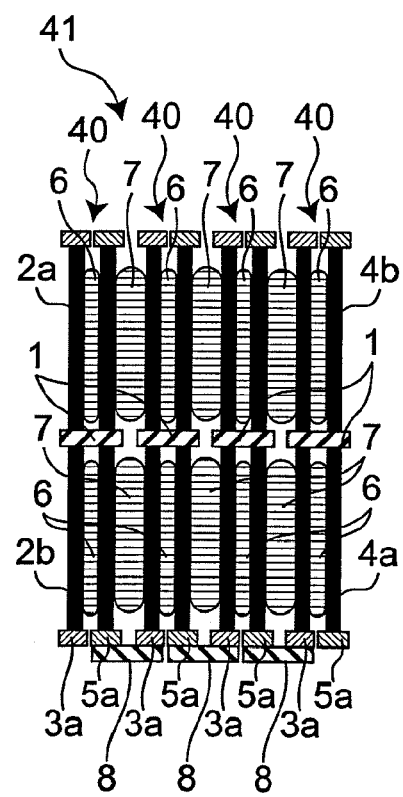
FIG. 4A is a cross-sectional view, taken along the cutting line similar to that of FIG. 2B, of a zero potential state (initial state) showing one example of a flat-plate lamination-type conductive polymer actuator device of a second embodiment of the present invention.

FIG. 4A shows flat-plate lamination-type polymer actuators 40 shown in FIG. 2B already described, which are laminated in parallel with each other with electrolyte holding layers 7 each being interposed therebetween, and the adjacent fixed frames 3a and 5 on one of the sides of the adjacent polymer actuators 40 are secured and coupled to each other by fixed frame coupling members 8 each made of an electrically insulating member. In this case, electrode wiring to the respective conductive polymer films is not illustrated because it is the same as that of FIG. 3A, which is characterized similarly to the first embodiment in that the face to face alignment is provided and in that the electrodes of the adjacent conductive polymer films are disposed so as to be always reversed to each other. The fixed frame coupling member 8 has a rod shape, and any desired member may be used as long as it functions to secure the adjacent fixed frames 3a and 5 on one of the sides of the adjacent polymer actuators 40.

Figure 4B:
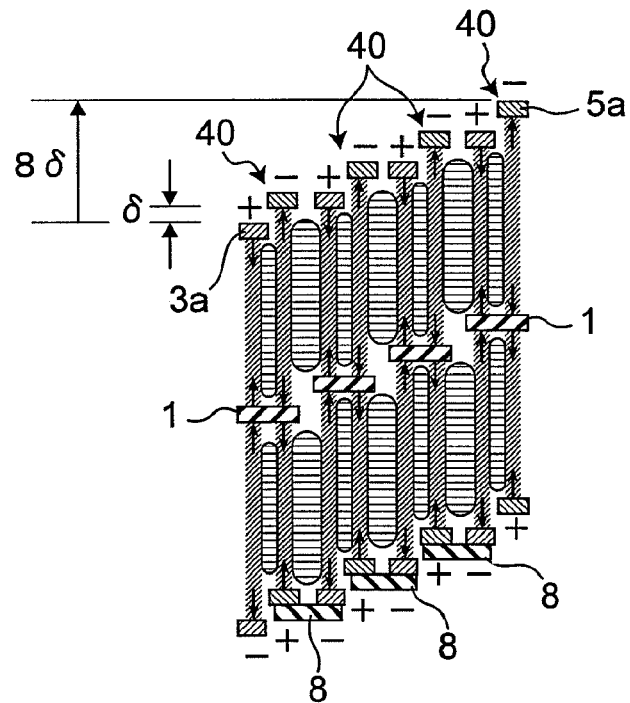
FIG. 4B is a cross-sectional view, taken along a cutting line similar to that of FIG. 2B, of a certain potential state showing the one example of the flat-plate lamination-type conductive polymer actuator device of the second embodiment of the present invention shown in FIG. 4A.
Figure 4C:
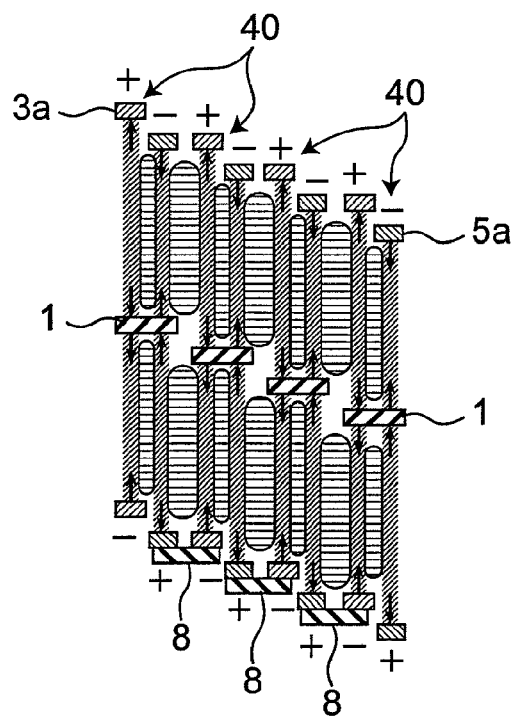
FIG. 4C is a cross-sectional view, taken along a cutting line similar to that of FIG. 2B, of a potential state reversed relative to that of FIG. 4B, showing the one example of the flat-plate lamination-type conductive polymer actuator device of the second embodiment of the present invention shown in FIG. 4A.

FIG. 4B shows expansion and contraction of the respective conductive polymer films, that is, displacement of the respective conductive polymer films, upon application of a voltage to each of the conductive polymer films. FIG. 4C shows an electric potential reversed relative to that of FIG. 4B. In either of the cases, similarly to the flat-plate lamination-type conductive polymer actuator according to the first embodiment, due to the structure in which the conductive polymer films are made face to face with each other each exerting rigidity and a driving force bidirectionally in the expanding direction and the contracting direction and being contracted and expanded with the electrolyte holding layers 6 and 7 respectively interposed therebetween, it is possible to carry out a driving operation efficiently while saving energy and space.

In FIGS. 4A to 4C, the electrolyte holding layers are illustrated as being larger in thickness in comparison with that of the electrolyte holding layers 6; however, the present invention is not limited thereto. As described earlier, similarly to the electrolyte holding layer 6, the thickness of the electrolyte holding layer 7 is preferably set in a range of approximately from 5 μm to 50 μm, and in a case of the thickness of the electrolyte holding layer 7 exceeding 50 μm, it is not possible to closely dispose the conductive polymer films. In contrast, in a case of the thickness of the electrolyte holding layer 7 less than 5 μm, the number of ions contained in the electrolyte holding layer 7 is smaller, with a result that a driving force or the amount of displacement is lowered.

In one specific example according to the second embodiment, the conductive polymer films 2a, 2b, 4b, and 4a each having a thickness of 15 μm are used, and the electrolyte holding layers 6 each having a thickness of 30 μm and the electrolyte holding layers 7 each having a thickness of 50 μm are used. Originally, from the viewpoint of commonly using components upon production, the electrolyte holding layers 6 and the electrolyte holding layers 7 should have the same thickness. However, in this case, each of the fixed frames 5a is supported by the fixed frame coupling member 8 by one side (in such a state where only the lower side of the fixed frame 5a shown in FIG. 4A is supported by the fixed frame coupling member 8), with a result that the side of the fixed frame 5a not supported by the fixed frame coupling member 8 (such as the upper side of the fixed frame 5a of FIG. 4A which is not supported by the fixed frame coupling member 8) becomes highly unstable; consequently, there is a possibility that the adjacent fixed frames 5a are separated from each other by a fine distance while being driven, so that the electrolyte holding layers 7 are prepared to have a thickness slightly larger than the thickness of the electrolyte holding layers 6 so as to flexibly deal with expansion of the gap between (so as to accept separation by a fine distance).

As shown in FIG. 4B, the amount of displacement with respect to the fixed frames on the two ends (the fixed frame 3a on the left end and the fixed frame 5a on the right end of FIG. 4B) corresponds to a value obtained by multiplying the amount of displacement δ of one of the conductive polymer films by the number of the conductive polymer films to be contracted. In the cases of FIGS. 4B and 4C, the number of the conductive polymer films to be contracted is eight, so that the amount of such displacement is as high as eight times (8×δ). The driving force is about one time of a driving force of one of the conductive polymer films, that is, equal thereto.

In a case of an actuator or an actuator device that utilizes not only the driving force or the amount of displacement with respect to the fixed frames on the two ends (the fixed frame 3a on the left end and the fixed frame 5a on the right end of FIG. 4B), but also the driving forces or the amounts of displacement with respect to a plurality of intermediate fixed frames, it is possible to realize such an actuator or an actuator device by arbitrarily setting the type or the dimension of each of the conductive polymer films, the electric potential to be applied to each of the conductive polymer films, or the types, the amount, or the like of the electrolyte holding layers.

Figure 4D:
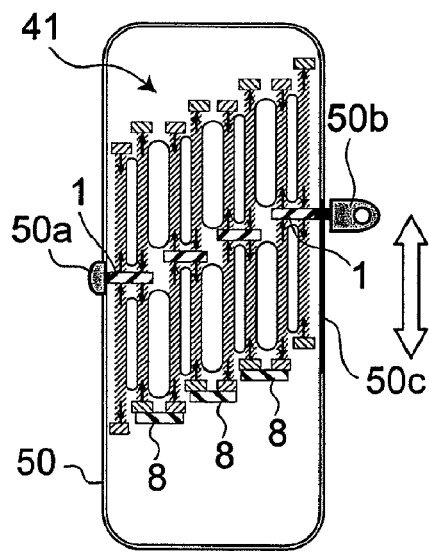
FIG. 4D is a cross-sectional view, taken along a cutting line similar to that of FIG. 2B, of a zero potential state (initial state) showing one example of a flat-plate lamination-type conductive polymer actuator device in accordance with a modified example of the second embodiment of the present invention.

FIG. 4D shows the flat-plate lamination-type conductive polymer actuator 40 installed in a casing 50, having one example of a structure in which a driving force or an amount of displacement is taken out of the link member 1 on one side. Specifically, the flat-plate lamination-type conductive polymer actuator device 41 according to the second embodiment shown in FIG. 4A is placed in the casing 50, and the link member 1 of the polymer actuator 40 on one of the ends (such as the left end of FIG. 4D) is secured to the casing 50 by a securing member 50a, while an output member 50b being connected to the link member 1 of the polymer actuator 40 on the other end (such as the right end of FIG. 4D). The output member 50b is designed to be movable due an opening 50c of the casing 50. Therefore, in the flat-plate lamination-type conductive polymer actuator device 41 according to the second embodiment shown in FIG. 4A, it is possible to take out the driving force or the amount of displacement of the flat-plate lamination-type conductive polymer actuator device 41 from the output member 50b connected to the link member 1 of the polymer actuator 40 on the other end (such as the right end of FIG. 4D).

Figure 4E:
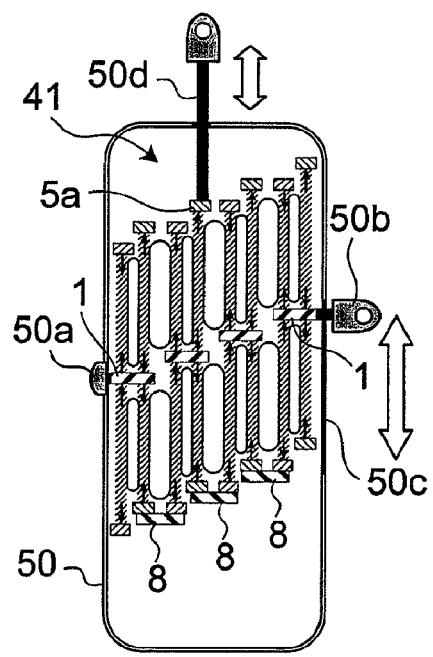
FIG. 4E is a cross-sectional view, taken along a cutting line similar to that of FIG. 2B, of a zero potential state (initial state) showing one example of a flat-plate lamination-type conductive polymer actuator device in accordance with another modified example of the second embodiment of the present invention.

FIG. 4E shows one example of a structure in which, in addition to the above-mentioned link member 1 on one of the sides, the driving force or the amount of displacement is taken out of an intermediate fixed frame 5a (such as the fourth fixed frame 5a from the left end of FIG. 4E). More specifically, in addition to the structure of FIG. 4D, a rod-shaped coupling member 50d that is movable through the casing 50 is secured to the fourth fixed frame 5a from the left end of FIG. 4E, and the coupling member 50d is allowed to move relatively to the casing 50 integrally with the fixed frame 5a in the longitudinal direction so that the driving force or the amount of displacement of the flat-plate lamination-type conductive polymer actuator device 41 can be taken out. The driving force or the amount of displacement to be taken out by the coupling member 50d is about a half as much as the amount of displacement taken out of the output member 50b of FIG. 4D, while the driving force being the same.

Figure 4F:
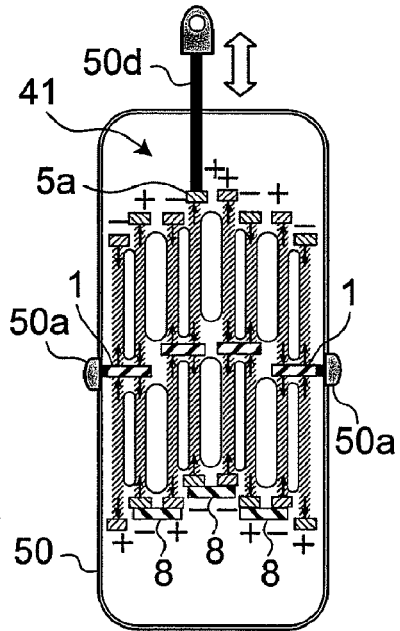
FIG. 4F is a cross-sectional view, taken along a cutting line similar to that of FIG. 2B, of a certain potential state showing one example of the flat-plate lamination-type conductive polymer actuator device in accordance with still another modified example of the second embodiment of the present invention.

FIG. 4F shows one example of a structure in which the driving force or the amount of displacement is taken out only from the intermediate fixed frame 5a (such as the fourth fixed frame 5a from the left end of FIG. 4E). More specifically, the link member 1 of the polymer actuator 40 on the other end (such as the right end of FIG. 4D) is also secured to the casing 50 by the securing members 50a. In this case, only the coupling member 50d is allowed to move relatively to the casing 50 so that the driving force or the amount of displacement of the flat-plate lamination-type conductive polymer actuator device 41 can be taken out. As will be described later, FIG. 4F shows a voltage applying method in a case where voltage applying patterns of FIG. 4B and FIG. 4C are combined with each other, in which, although the amount of displacement in the driving operation in the center to be taken out from the output member 50b of FIG. 4D is the same as that of FIG. 4E, two times as much driving force as that of FIG. 4E can be taken out from the output member 50b of FIG. 4D.

Any of the above structures are included in the present invention.

As described above, by the structure that exerts rigidity and a driving force bidirectionally in the contracting direction and the expanding direction and can expand displacement by lamination with a high density, with the expanding and contracting conductive polymer films 2a, 2b, 4b, and 4a being aligned face to face with each other with the electrolyte holding layers 6 and 7 interposed therebetween, respectively, it becomes possible to obtain a flat-plate lamination-type conductive polymer actuator device 41 capable of carrying out a driving operation efficiently while saving energy and space.

Third Embodiment

Figure 5A:
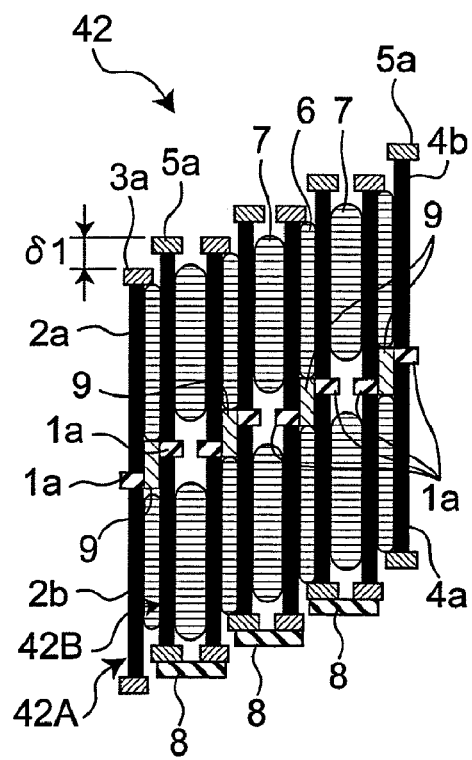
FIG. 5A is a cross-sectional view, taken along a cutting line similar to that of FIG. 2B, of a zero potential state (initial state) showing one example of a flat-plate lamination-type conductive polymer actuator device of a third embodiment of the present invention.

FIG. 5A is a view showing a zero electric potential state (initial state) in one example of a flat-plate lamination-type conductive polymer actuator device 42 in accordance with a third embodiment of the present invention, that is a cross-sectional view taken along the same cutting line as that of FIG. 2B. In the flat-plate lamination-type conductive polymer actuator device 42 of FIG. 5, different from the flat-plate lamination-type conductive polymer actuator device 40 shown in FIG. 4A, upon lamination, a coupling process can be carried out on the link member 1 so as to preliminarily apply a displacement $\delta_1$ thereto, so as to set the displacement between the fixed frames to zero in a charge-applied state, and in this structure, a deformation link member 9 made of a non-insulating member that is electrically conductive is used. In each of the four flat-plate lamination-type conductive polymer actuators 40 of the flat-plate lamination-type conductive polymer actuator device 41 of the second embodiment shown in FIG. 4A, one end of the plate-shaped link member 1 prepared as a plate-shaped rectangular parallelepiped member is connected to the conductive polymer films 2a and 2b, and the other end is connected to the conductive polymer films 4b and 4a. In contrast, each of the four flat-plate lamination-type conductive polymer actuators of the flat-plate lamination-type conductive polymer actuator device 42 of the third embodiment differs from the flat-plate lamination-type conductive polymer actuator 40 in that the conductive polymer films 2a and 2b of the first actuator unit 42A are connected to each other, for example, through an insulating link member 1a having a rectangular parallelepiped rod-shape, with the conductive polymer films 4b and 4a of the second actuator unit 42B being connected to each other, for example, through a link member 1a having a rectangular parallelepiped rod-shape, so that two link members 1a are prepared, and in that, as shown in FIG. 5A, these two adjacent link members 1a are preliminarily coupled to each other by the deformation link member 9 in a deviated state with the displacement $\delta_1$ between upper and lower positions. Similarly to the first actuator unit 40A and the second actuator unit 40B of the first embodiment, the first actuator unit 42A and the second actuator unit 42B are allowed to sandwich the electrolyte holding layer 6. In a case where four actuators, each formed by the first actuator unit 42A and the second actuator unit 42B, are disposed in parallel with one another, the electrolyte holding layer 7 is sandwiched in each of the gaps between the actuators, similarly to the second embodiment.

More specifically, the deformation link member 9 is made of, for example, a rod-shaped member having a rectangular parallelepiped shape. On the side face on the lower left side end of this deformation link member 9, a left-end link member 1a, as shown in FIG. 5A, is secured, and on the side face on the upper right side end of the deformation link member 9, the second link member 1a from the left end of FIG. 5A is secured. Similarly to the link member 1, the link member 1a is also preferably made of an insulating material.

In FIGS. 4A to 4C, the fixed frame 5a on the other end relative to one of the fixed frames 3a is greatly displaced in two directions depending on the negative or positive phase of an applied voltage, in comparison with the state where the electric potential is set to zero. However, depending on the usage, it is supposed that there is a case where the displacement of the fixed frames 3a and 5a is preferably limited to only one direction, even application of positive and negative voltages.

Figure 5B:
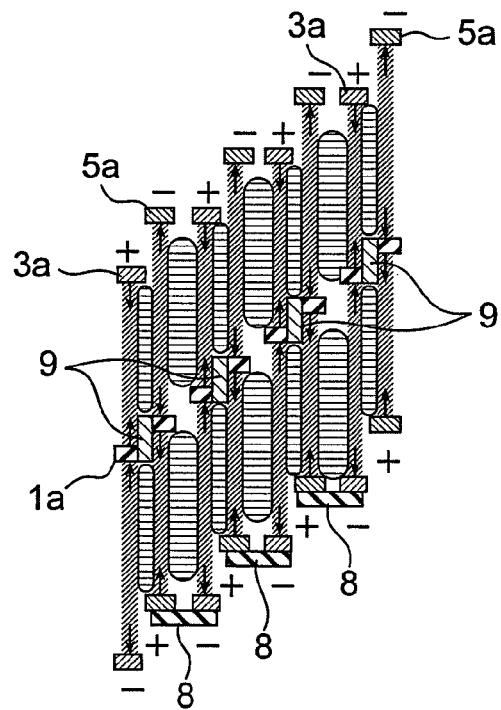
FIG. 5B is a cross-sectional view, taken along a cutting line similar to that of FIG. 2B, of a certain potential state showing the one example of the flat-plate lamination-type conductive polymer actuator device of the third embodiment of the present invention shown in FIG. 5A.
Figure 5C:
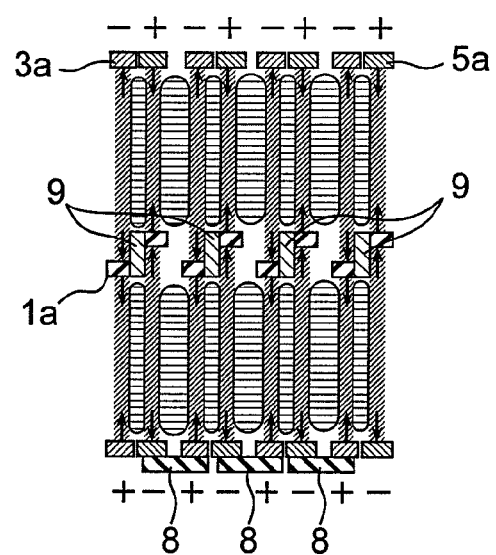
FIG. 5C is a cross-sectional view, taken along a cutting line similar to that of FIG. 2B, of a potential state that is reverse that of FIG. 5B, showing the one example of the flat-plate lamination-type conductive polymer actuator device of the third embodiment of the present invention shown in FIG. 5A.

Therefore, by using such a structure as shown in FIG. 5A, an arrangement may be prepared in which, as shown in FIG. 5B, although, upon application of a certain electric potential, a great displacement is generated in the fixed frames 3a and 5a, the displacement between the fixed frames 3a and 5a becomes zero, as shown in FIG. 5C, upon application of a charge reversed relative to that of FIG. 5B.

In completely the same manner as in the second embodiment, in the third embodiment also, by using a structure in which the conductive polymer films 2a and 3b, as well as 4b and 4a, that exert rigidity and a driving force bidirectionally, that is, in the contracting direction and the expanding direction, and have an expanded displacement only in one direction in a high-density laminated structure, are made face to face with each other, with the electrolyte holding layers 6 and 7 interposed therebetween, it becomes possible to provide a flat-plate lamination-type conductive polymer actuator device capable of carrying out a driving operation efficiently while saving energy and space. Depending on the space in which the flat-plate lamination-type conductive polymer actuator device of the third embodiment is installed, this structure is very effectively used in such a case (see FIG. 5C) where, although the driving displacement directed from the fixed frames 3a and 5a on the two ends is initially at the same position (see FIG. 5C), a large amount of displacement (see FIGS. 5B and 5C) is required at the time of driving.

Fourth Embodiment

Figure 6A:
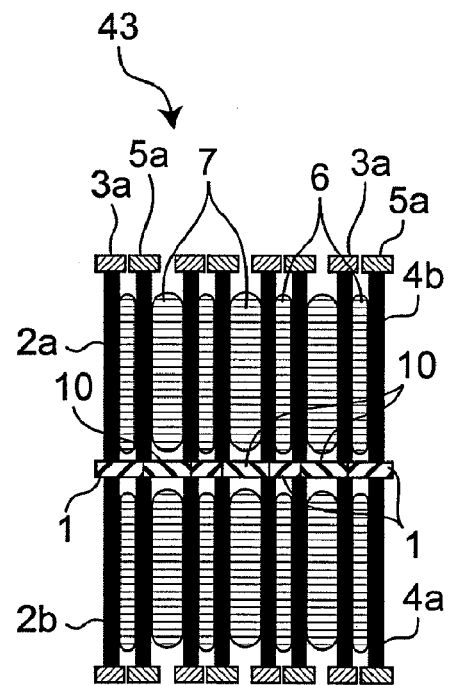
FIG. 6A is a cross-sectional view, taken along a cutting line similar to that of FIG. 2B, of a zero potential state (initial state) showing one example of a flat-plate lamination-type conductive polymer actuator device of a fourth embodiment of the present invention.

FIG. 6A is a view showing a zero electric potential state (initial state) in one example of a flat-plate lamination-type conductive polymer actuator device 43 in accordance with a fourth embodiment of the present invention, and is a cross-sectional view taken along the same cutting line as that of FIG. 2B. In FIG. 6A, upon laminating the flat-plate lamination-type conductive polymer actuators, shown in FIG. 2B, in parallel with one another and with the electrolyte holding layer 7 interposed therebetween, different from the structure shown in FIGS. 4A and 5A, the adjacent link members 1 are coupled to one other by using, for example, a link-member coupling member 10 that is an electrically insulating member and has a rectangular parallelepiped rod-shape. For example, such a coupled structure is preferably prepared as a structure in which, an engaging convex portion is formed on either one of the link-member coupling member 10 and the link member 1, with an engaging concave portion being formed in the other, so that, by engaging the engaging convex portion with the engaging concave portion, these members are detachably coupled to each other. A plurality of link-member coupling members 10 and a plurality of link members 1 may be formed by using a single rod-shaped member.

In the aforementioned second embodiment and third embodiment, an attempt is made to increase the amount of displacement mainly by laminating the conductive polymer actuators. The fourth embodiment is characterized in that an attempt is made to increase a stress by laminating the conductive polymer actuators. In the conventional structure, no stress magnification-means for obtaining the effect corresponding to the laminating method is prepared except for placing a plurality of bimorph-type actuators in parallel with one another, and, in particular, the structure of Patent Document 1 makes it difficult to carry out the laminating process.

Figure 6B:
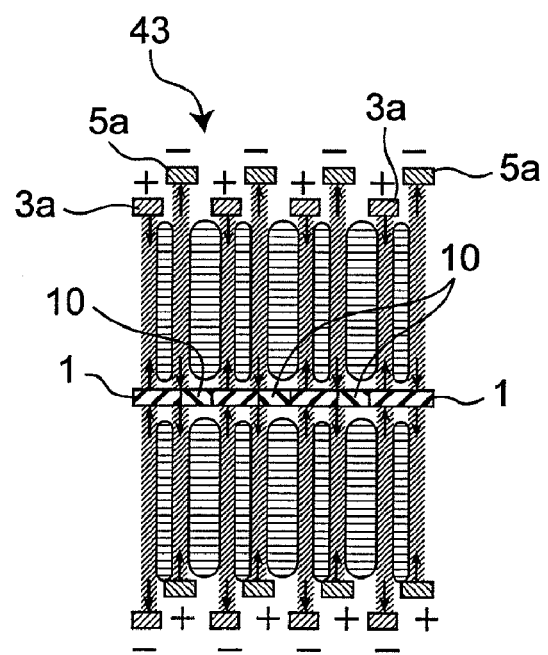
FIG. 6B is a cross-sectional view, taken along a cutting line similar to that of FIG. 2B, of a certain potential state showing the one example of the flat-plate lamination-type conductive polymer actuator device of the fourth embodiment of the present invention.
Figure 6C:
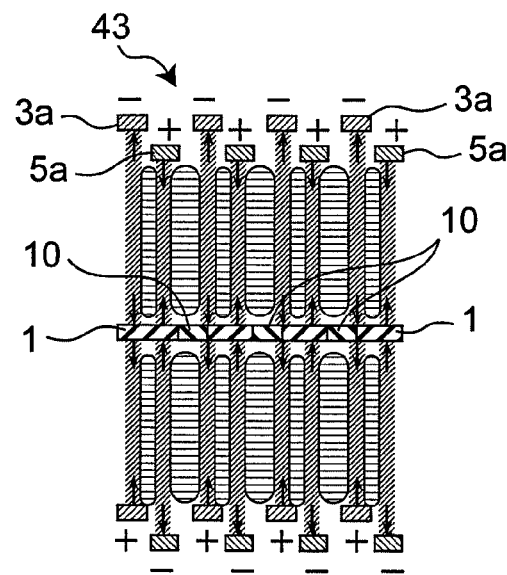
FIG. 6C is a cross-sectional view, taken along a cutting line similar to that of FIG. 2B, of a potential state reversed relative to that of FIG. 6B, showing the one example of the flat-plate lamination-type conductive polymer actuator device of the fourth embodiment of the present invention.

As shown in FIGS. 6B and 6C, the fixed frames 3a and 5a are displaced depending on the positive or negative state of the electrode. In this case, the amount of displacement in each of the fixed frames 3a and 5a is equal to the amount of displacement of one conductive polymer film because the adjacent link members 1 are coupled to each other by the link-member coupling member 10. However, the driving force is multiplied by the number of the conductive polymer films to be contracted. In the structure shown in FIGS. 6B and 6C, a driving force as high as eight times the driving force of one fixed frame (one conductive polymer film to be contracted) can be obtained as the total driving force of the four fixed frames 3a and 5a (four conductive polymer films to be contracted).

As described above, by providing a structure that exerts rigidity and a driving force bidirectionally in the contracting direction and the expanding direction and can obtain an expanded stress by using a high-density laminated structure, with the conductive polymer films 2a, 2b, 4b, and 4a that expand and contract being made face to face with each other, with the electrolyte holding layers 6 and 7 interposed therebetween, it becomes possible to obtain a flat-plate lamination-type conductive polymer actuator device 43 capable of carrying out a driving operation efficiently while saving energy and space. This structure is, in particular, effectively applied to a case where, although an increased amount of displacement is not required, a great stress is required.

(Modified Examples)

Among various embodiments as described above, by combining desired embodiments on demand, it becomes possible to obtain the respective effects thereof.

In the various embodiments, the following structures may be formed and the same effects as those of the present invention can be obtained.

In FIGS. 4A to 6C, voltages to be applied to the respective conductive polymer films 2a, 2b, 4b, and 4a are illustrated as being equal to one another; however, the present invention is not intended to be limited by this. For example, a method may be effectively used in which the conductive polymer film to which a voltage is applied is selected depending on a required stress or a required amount of displacement, or the polarity or the size of the voltage is appropriately adjusted for each of the conductive polymer films.

Although FIG. 4F shows a structure in which patterns of the applied voltages of FIGS. 4B and 4C are combined with each other, by respectively securing the link members 1 on the two ends to a casing 50 by using securing members 50a, for example, a structure can be formed in which, although the amount of displacement is the same in the center, the driving stress is increased to two times as large as that shown in FIG. 4E. The casing 50 may have an insulating property or a conductive property.

Figure 7A:
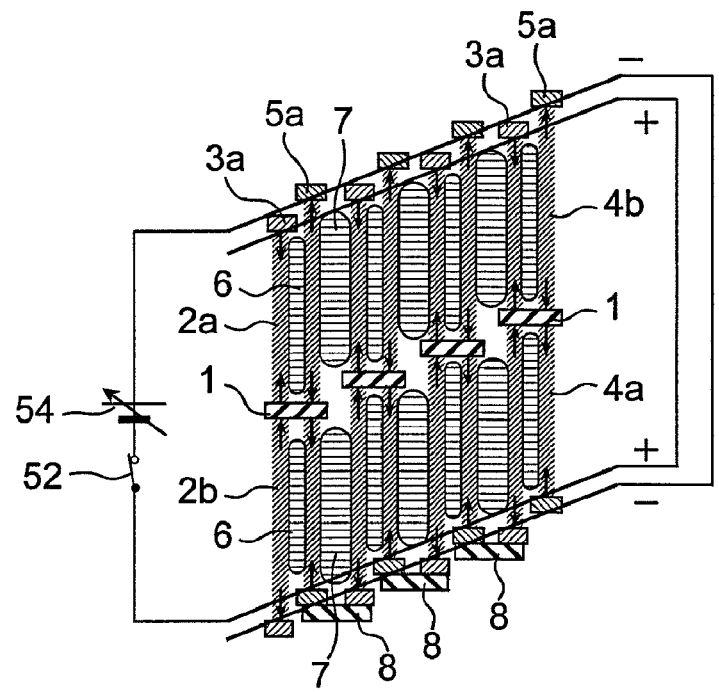
FIG. 7A is a view showing one example of wiring of the flat-plate lamination-type conductive polymer actuator device in accordance with the second embodiment of the present invention shown in FIG. 4A.
Figure 7B:
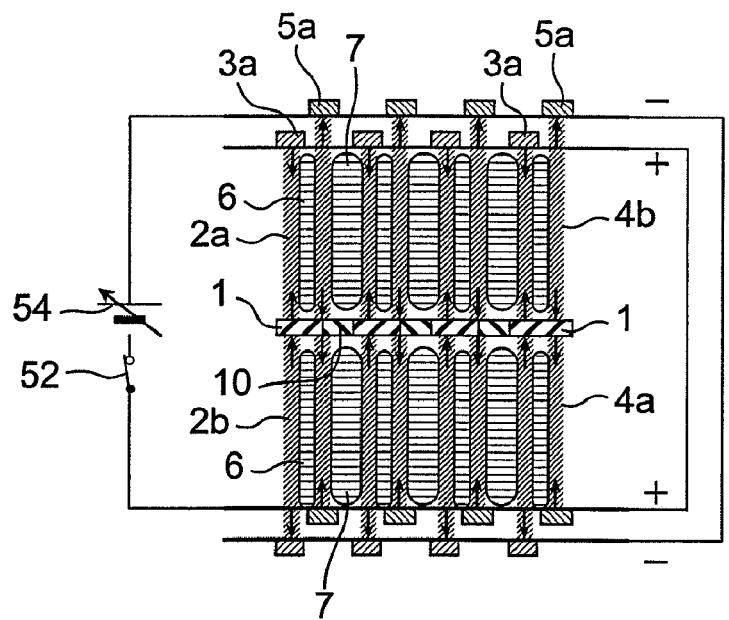
FIG. 7B is a view showing one example of wiring of the flat-plate lamination-type conductive polymer actuator device in accordance with the fourth embodiment of the present invention shown in FIG. 6A.

In a case of wiring structures as shown in FIGS. 7A and 7B, however, since it is difficult to select the conductive polymer film to which a voltage is applied, the wiring needs to be altered.

In a case of the electrolyte holding layer in the center of FIG. 4F, since the polarities of voltages to be applied to the conductive polymer films on the two sides are the same, it fails to sufficiently function. However, in each of the cases, the stress or the change in the amount of displacement can be controlled in response to a speed at which the voltage is applied.

In FIGS. 4A to 6C, with respect to all the faces, opposing or adjacent conductive polymer films are disposed so as to always have reversed electrodes; however, the present invention is not intended to be limited by this structure, depending on cases. However, in a case of a layout except for the layout in which the adjacent conductive polymer films always have reversed electrodes, the advantage that an effective driving operation is obtained, with energy and space being saved, is lowered.

Figure 6D:
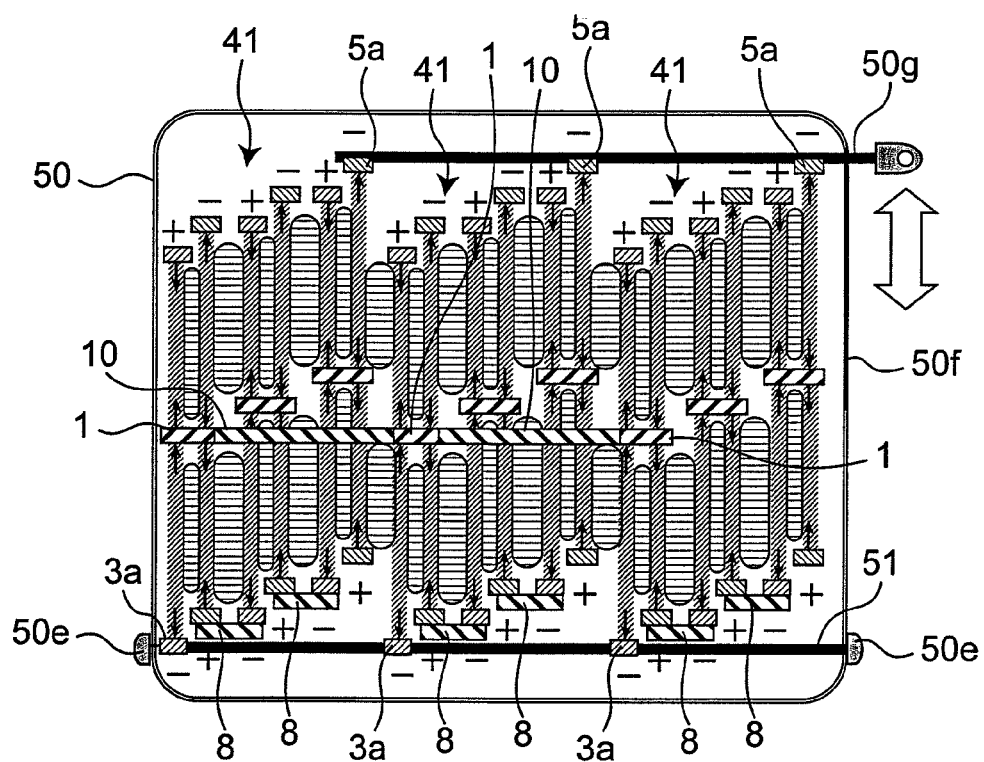
FIG. 6D is a cross-sectional view, taken along a cutting line similar to that of FIG. 2B, of a certain potential state showing one example of a flat-plate lamination-type conductive polymer actuator device of a modified example of the fourth embodiment of the present invention, in a case where the pattern of the structure of FIG. 4B and the pattern of the structure of FIG. 6B are combined with each other.

Furthermore, the structure to be used for expanding the displacement shown in FIGS. 4A and 5A and the structure to be used for expanding the stress shown in FIG. 6A only differ from each other in whether the actuators are laminated by using fixed-frame coupling members 8 or the actuators are coupled to one another by using link-member coupling members 10, and these structures may coexist. For example, FIG. 6D shows a structure in which the pattern of the structure of FIG. 4B and the pattern of the structure of FIG. 6B are combined with each other, and, for example, an arrangement may be proposed in which the driving stress is increased to three times, and the amount of displacement is increased to six times, in comparison with the structure with one sheet of the conductive polymer film to be contracted. In the structure of FIG. 6D, in place of the link-member coupling member 10, by using a casing securing member 51 for securing the casing 50 and the fixed frame 3a so as to be located below the flat-plate lamination-type conductive polymer actuator 41 of the second embodiment, as shown in the drawing, the conductive polymer actuators 41 are coupled to one another so that the function of the link-member coupling member 10 can be substituted. The casing securing member 51 may have an insulating property or a conductive property. In this case, the casing securing member 51 is made of a rod-shaped member, and is fixedly coupled to the fixed frame 3a on the left end of FIG. 6D of each of the conductive polymer actuator devices 41, with its two ends being respectively secured to the casing 50 by securing members 50e. Since the other fixed frames 5a and 3b of each of the conductive polymer actuator devices 41 are not secured to the casing securing member 51, they are allowed to be movable. On the other hand, an output shaft member 50g is placed above each of the conductive polymer actuator devices 41. The output shaft member 50g may have an insulating property or a conductive property. The output shaft member 50g, made of a rod-shaped member, is placed at the opening 50f of the casing 50 so as to be movable upward and downward in FIG. 6D. The output shaft member 50g is fixedly coupled to the fixed frame 5a on the right end of FIG. 6D of each of the conductive polymer actuator devices 41 so as to take the driving force and amount of displacement out of each of the conductive polymer actuator devices 41. The link members 1 on the left end of the respective conductive polymer actuator devices 41 are fixedly coupled to one another by using the link-member coupling members 10.

In any of these cases, both of the link-member coupling members 10 and the casing securing members 51 need to be disposed outside of the fixed frames 3a and 5a in structures thereof in order to avoid collision with the conductive polymer films 2a, 2b, 4b and 4a. In this case, FIG. 6D shows the conductive polymer films 2a, 2b, 4b and 4a so as to emphasize the thickness direction thereof (illustrated with the size in the thickness direction being enlarged in comparison with that in the longitudinal direction); however, actually, the size in the thickness direction is, for example, only about 1 mm or less even after the actuators have been laminated, while the size in the longitudinal direction is, for example, about 5 mm or more. That is, by carrying out a lamination process so as to properly combine the actuators, in response to the driving force required and the amount of displacement required in accordance with the application field, a most suitable flat-plate lamination-type conductive polymer actuator device can be freely formed, and this point forms another great advantage.

Upon coupling the adjacent fixed frames 5a and 3a with each other in the adjacent actuators by using the fixed-frame coupling members 8 (see FIG. 4A), as shown in FIG. 7A, as well as upon coupling the link members 1 with each other by using the link-member coupling members 10 (see FIG. 6A), as shown in FIG. 7B, the wiring can be formed by using a substantially linear electrode. In these actuators, since the expanding conductive polymer film and the contracting conductive polymer film are disposed alternately, the wiring of the electrodes appears to be very difficult. However, judging from the layout of the fixed frames 3a and 5a at the time of driving, these structures are advantageous in that the substantially linear electrode can be used, as shown in FIGS. 7A and 7B, and in that the manufacturing process can be, in particular, simplified greatly.

Figure 8A:
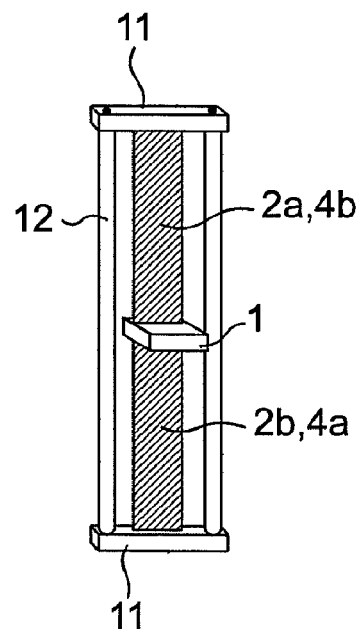
FIG. 8A is a perspective view showing one example of an outer appearance of a flat-plate lamination-type conductive polymer actuator in accordance with another embodiment of the present invention.
Figure 8B:
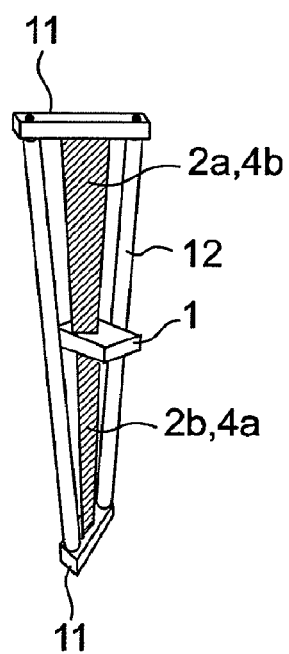
FIG. 8B is a perspective view showing a state where the flat-plate lamination-type conductive polymer actuator of FIG. 8A is twisted.
Figure 8C:
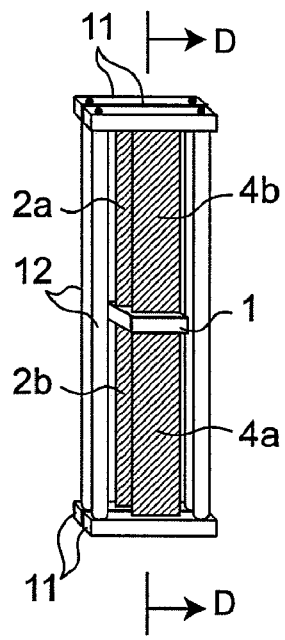
FIG. 8C is a perspective view showing a state where a flat-plate lamination-type conductive polymer actuator is configured by laminating two flat-plate lamination-type conductive polymer actuators of FIG. 8A.
Figure 8D:
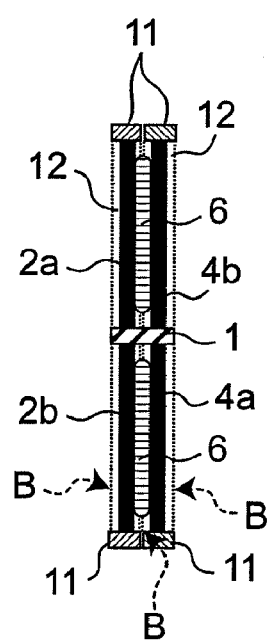
FIG. 8D is a cross-sectional view, taken along line D-D of FIG. 8C, showing the flat-plate lamination-type conductive polymer actuator of FIG. 8C.

In place of the fixed frames 3a and 5a, as shown in FIG. 8A, a two-end fixed frame 11 and a flexible fixed frame 12 may be used. That is, fixed frames 11, each made of a rigid member, are secured to the upper and lower ends of FIG. 8A of a flexible fixed frame 12 having a square frame shape made of a flexible material so that this structure is formed, and since the flexible fixed frame 12 exerts pliability, this structure can be freely twisted. In this structure, only the expanding direction of the conductive polymer films 2a, 2b, 4b and 4a is regulated by the two-end fixed frame 11 and the flexible fixed frame 12 so as to prevent the conductive polymer films 2a, 2b, 4b and 4a from being buckled, and, as shown in FIG. 8, the twisting direction may be left freely. As a result, as shown in FIG. 8C, from the basic structure of the flat-plate lamination-type conductive polymer actuator shown in FIG. 8A, another actuator may be proposed in which, in addition to the structure of the flat-plate lamination-type conductive polymer actuator formed by laminating two flat-plate lamination-type conductive polymer actuators of FIG. 8A, a structure that has a soft string shape, and is resistant to twisting operations is prepared. Consequently, in a case where the actuator is placed along an object having a curved shape or when an external force is applied to the face of the conductive polymer film of the actuator in a direction perpendicular thereto, the actuator having the above-mentioned structure is very effectively used. For example, upon placing the actuator along the periphery of an artificial bone as an artificial muscle, the flat-plate lamination-type conductive polymer actuator as shown in FIG. 8A can be easily placed even at complicated positions, and since it exerts a flexible characteristic against the external force as the artificial muscle, the actuator becomes closer to the human muscle. In a case where the two-end fixed frame 11, made in contact with the conductive polymer films 2a, 2b, 4b and 4a, has a conductive property, with the other portions of the flexible fixed frame 12 being made of an insulating member, a wiring process is required for each of the aforementioned conductive polymer films; however, this structure allows the wiring to be made on a portion of the fixed frame having the conductive property (on the two-end fixed frame 11), making it possible to further simplify and ensure the manufacturing process. It is also possible to improve the reliability to the wiring portion at the time of driving. In this case also, different from the cases shown in FIGS. 2A, 2B and 2C, since the structures of the spacers 3b and 5b become complicated, this structure is prepared on the premise that the flexible fixed frames 12 in FIG. 8C are mutually made adjacent to one another and in contact with one another. In FIG. 8D that corresponds to a cross-sectional view taken along line D-D of FIG. 8C, as indicated by a broken line B in FIG. 8D, the flexible fixed frames 12 need to be mutually made in contact with, and adjacent to each other. In the fixed frames 3a and 5a also, the upper and lower ends may be formed by a conductive member, with the other frame portions, such as pillar portions along the upward and downward directions that couple the upper and lower ends with each other, being made by an insulating material; thus, the same advantages as described above can be obtained.

Figure 9:
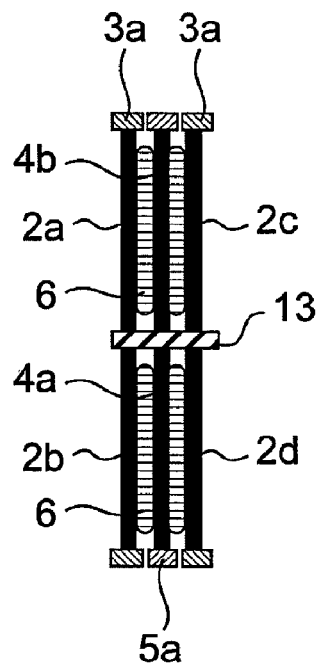
FIG. 9 is a cross-sectional view taken along a cutting line similar to that of FIG. 2B, showing one example of a flat-plate lamination-type conductive polymer actuator device in accordance with still another embodiment of the present invention.

As shown in FIG. 9, in addition to the first to fourth conductive polymer films 2a, 2b, 4b and 4a, insulating continuous link members 13 may be formed as fifth and sixth conductive polymer films 2c and 2d and a third link member so that it is possible to suppress torques to be exerted on the first link member 1 (see FIG. 3B), with its one end (such as the left end of FIG. 9) being connected to the first and second conductive polymer films 2a and 2b and the other end (such as the right end of FIG. 9) being connected to the third and fourth conductive polymer films 4b and 4a, as well as on the second link member 1, with its one end (such as the left end of FIG. 9) being connected to the third and fourth conductive polymer films 4b and 4a and the other end (such as the right end of FIG. 9) being connected to the fifth and sixth conductive polymer films 2c and 2d (refer to states in which, in FIG. 3C, the first and second conductive polymer films 2a and 2b are replaced by the third and fourth conductive polymer films 4b and 4a, with the third and fourth conductive polymer films 4b and 4a being replaced by the fifth and sixth conductive polymer films 2c and 2d). That is, without the continuous link members 13, the first link member 1, placed in a bridged manner between the first and second conductive polymer films 2a, 2b and the third and force conductive polymer films 4b, 4a, would generate a torque so as to rotate anticlockwise, because, as shown in FIG. 3B, the first and fourth conductive polymer films 2a and 4a contract while the second and third conductive polymer films 2b and 4b expand. In contrast, without the continuous link members 13, the second link member 1, placed in a bridged manner between the third and fourth second conductive polymer films 4b, 4a and the fifth and sixth conductive polymer films 2c, 2d, would generate a torque so as to rotate clockwise, because the fourth and sixth conductive polymer films 4a and 2c contract while the third and fifth conductive polymer films 4b and 2d expand. Therefore, by coupling the first link member 1 and the second link member 1 by using the continuous link member 13, the torques are made to cancel each other so that the torques can be suppressed. The fifth and sixth conductive polymer films 2c and 2d are respectively the same as the conductive polymer films 2a and 2b. For example, upon functioning as actuators that generate stresses in FIG. 3B, stresses in reversed directions are exerted on the first link member 1 and the second link member 1 in the directions in parallel with the face of the conductive polymer film. Therefore, as shown in FIG. 9, by installing the continuous link members 13 that are connected to the first link member 1 and the second link member 1, and allowed to function the third link members, a structure in which no torque toward the continuous link members 13 is generated can be realized. This structure is very effective for such a case for increasing the stress.

Figure 10:
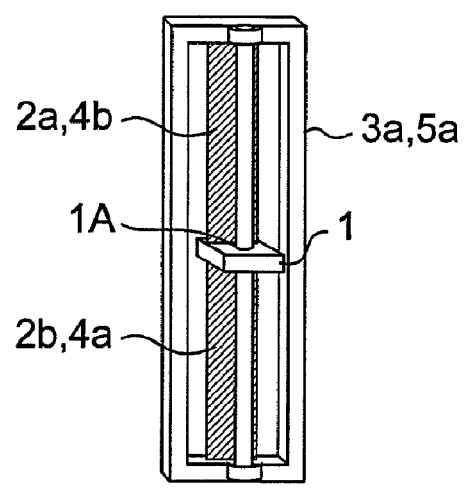
FIG. 10 is a perspective view showing one example of a flat-plate lamination-type conductive polymer actuator in accordance with still another embodiment of the present invention.

FIG. 10 shows a structure that is used for limiting movements of the first and second link members 1 in a direction perpendicular to the longitudinal direction of the conductive polymer films 2a, 2b, 4b and 4a, against the torque generated in the first and second link members 1 or an external force exerted in a direction perpendicular to the longitudinal direction of the conductive polymer films 2a, 2b, 4b and 4a. That is, in this structure, a rod 15 is disposed on the first fixed frame 3a or the second fixed frame 5a in the longitudinal direction thereof, with the two ends of the rod 15 being fixedly supported on the upper and lower two ends of the first fixed frame 3a or the second fixed frame 5a, and an opening 1A is formed in the first link member 1 or the second link member 1 so as to allow the first link member 1 or the second link member 1 to be movable relative to the rod 15 so that the rod 15 is made to penetrate the opening 1A. With this arrangement, the first and second link members 1 are allowed to move only in a direction along the longitudinal direction of the rod 15, relative to the first fixed frame 3a or the second fixed frame 5a. This structure allows the function corresponding to the flexible fixed frame 12 in the structure as shown in FIGS. 8A and 8D to be also exerted on the conductive polymer films 2a, 2b, 4b and 4a. That is, by the movement of the link member 1 in the thickness direction of the conductive polymer films 2a, 2b, 4b and 4a, an effect for preventing the adjacent conductive polymer films 2a and 4b from being made in contact with each other, or the adjacent conductive polymer films 2b and 4a from being made in contact with each other, so that it is possible to effectively prevent an electrical short circuit, and consequently to ensure a stable driving operation.

Figure 11:
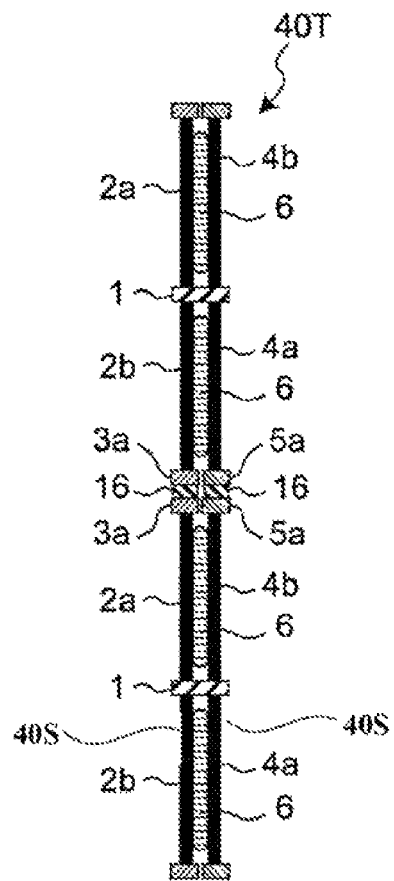
FIG. 11 is a cross-sectional view, taken along a cutting line similar to that of FIG. 2B, showing one example of a flat-plate lamination-type conductive polymer actuator device in accordance with still another embodiment of the present invention.

Differently from FIGS. 4A, 5A and 6A, FIG. 11 shows a flat-plate lamination-type conductive polymer actuator device 40T having a structure in which a plurality of actuators are laminated in a direction along the faces of the conductive polymer films 2a, 2b, 4b and 4a. That is, flat-plate lamination-type conductive polymer actuators 40S, shown in FIGS. 2D and 2E, are laminated and disposed in the longitudinal direction, and the fixed frame 3a on the lower end of the upper flat-plate lamination-type conductive polymer actuators 40S and the fixed frame 3a of the upper end of the lower flat-plate lamination-type conductive polymer actuators 40S are coupled by an insulating fixed frame coupling member 16, with the fixed frame 5a on the lower end of the upper flat-plate lamination-type conductive polymer actuators 40S and the fixed frame 5a of the upper end of the lower flat-plate lamination-type conductive polymer actuators 40S being coupled by an insulating fixed frame coupling member 16. The fixed frame coupling member 16 is, for example, made of a rectangular parallelepiped rod member, or the like. For example, in a case where, upon forming a single conductive polymer film, the size to be manufactured is limited, or in a case where elasticity needs to be properly prepared against an external force applied in a direction perpendicular to the longitudinal direction of the conductive polymer films 2a, 2b, 4b and 4a, the flat-plate lamination-type conductive polymer actuator device 40T having the structure shown in FIG. 11 provides an effective structure. Of course, the structure of the flat-plate lamination-type conductive polymer actuator device 40T, shown in FIG. 11, is a structure which, in the same manner as shown in FIGS. 4A to 6D, allows a flat-plate lamination-type conductive polymer actuator device 40T having another structure of FIG. 11 to be simultaneously laminated thereon in a direction perpendicular to the faces of the conductive polymer films 2a, 2b, 4b and 4a. That is, a large number of single films having not a long dimension, but a short dimension, can be produced and utilized as the conductive polymer actuator devices 40T so that it is possible to improve the production efficiency, or to disperse an external force applied to the conductive polymer films 2a, 2b, 4b and 4a; thus, it becomes possible to provide an effect for enhancing toughness as the product.

It has been known that the conductive polymer films 2a, 2b, 4b and 4a have such a characteristic that they are expanded or contracted upon application of a voltage, while, in contrast, they also generate power when expanded or contracted. Therefore, the laminated actuator fixed frames 3a and 5b, as shown in FIGS. 4A to 6D, are made in contact with a face having a complex shape, and the laminated actuators are pressed onto the face having the complex shape so that the fixed frames 3a and 5b are positioned along the face having the complex shape. As a result, based upon a voltage distribution caused by power from the laminated actuators, the complex shape can be taken out as electronic information so that the application as a shape sensor can also be effectively provided. Of course, even when such a structure as an actuator unit 40A that only has half the flat-plate lamination-type conductive polymer actuators shown in FIG. 1A is used, this can be utilized to sense the position of the first link member 1 so that the application as a position sensor for use in one-dimensional bidirections, without the necessity of a preliminary pressure application conventionally required, can be effectively achieved.

As the electrolyte holding layers 6 and 7 illustrated between the conductive polymer films 2a, 2b, 4b and 4a, a gel-state ionic liquid is used, and these are only made in contact with the conductive polymer films 2a, 2b, 4b and 4a, and supposed to be deformed or allowed to slide in response to expansion or contraction of the conductive polymer films 2a, 2b, 4b and 4a. Even not a gel-state structure, but a structure in which the entire flat-plate lamination-type conductive actuators are immersed in an ionic liquid is used, the same effects can be obtained.

Each of the first and second fixed frames 3a and 5a may have a structure integrally formed with the gel-state ionic liquid. Although the gel-state ionic liquid is easily deformed, a supporting member corresponding to the fixed frame can be formed therein like a backbone. In this case, the number of the constituent members of the flat-plate lamination-type conductive actuator can be reduced so that the production process can also be simplified.

The above description is based on the premise that, in a manner reversed relative to the structure of Patent Document 1, cations are inserted into the conductive polymer film to cause the conductive polymer film to be expanded, while, in contrast, anions are removed from the conductive polymer film to cause the conductive polymer film to be contracted. However, depending on the kinds of the conductive polymer film or the kinds of the ionic liquid or the combinations thereof, the same phenomenon is caused not by cations, but by anions as in the case of Patent Document 1. In this case also, the same effects can be obtained by the present invention.

Fifth Embodiment

Figure 15A:
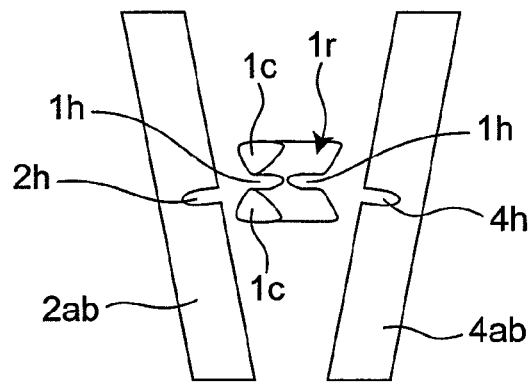
FIG. 15A is an exploded explanatory view showing a flat-plate lamination-type conductive polymer actuator in accordance with a fifth embodiment of the present invention.
Figure 15B:
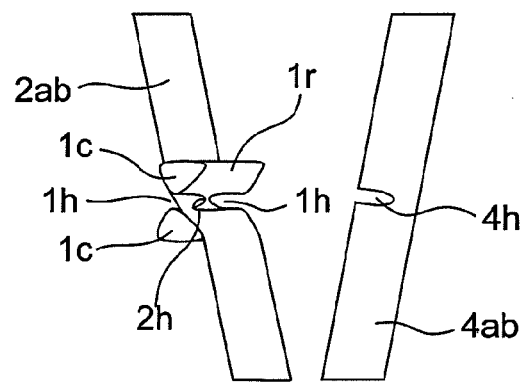
FIG. 15B is an exploded explanatory view of the flat-plate lamination-type conductive polymer actuator of FIG. 15A being partially assembled.
Figure 15C:
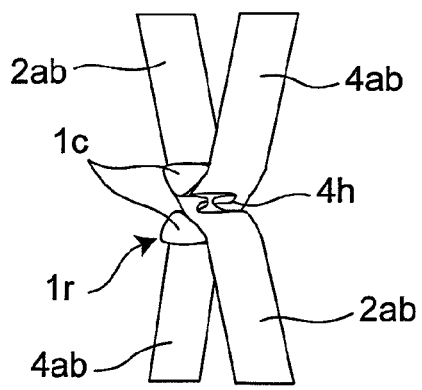
FIG. 15C is an explanatory view of the flat-plate lamination-type conductive polymer actuator of FIG. 15A being assembled.
Figure 15D:
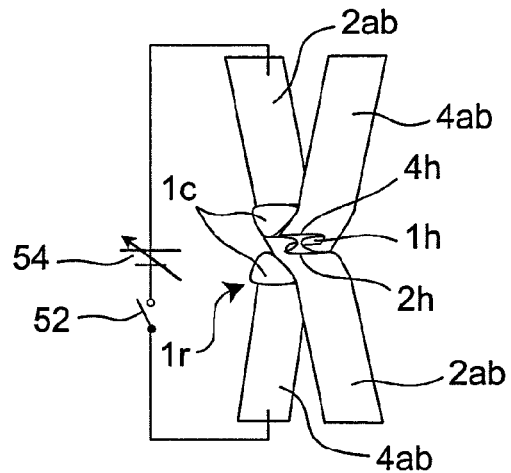
FIG. 15D is an explanatory view of a state where wiring is further attached to the flat-plate lamination-type conductive polymer actuator of FIG. 15C.
Figure 15E:
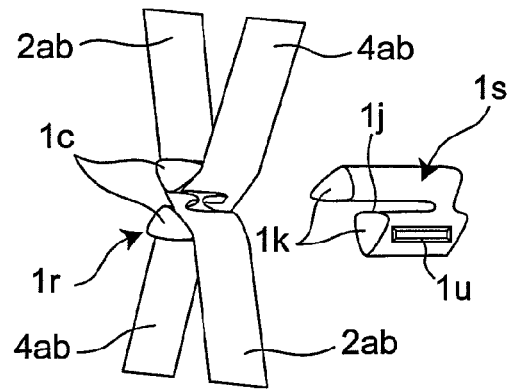
FIG. 15E is an exploded explanatory view showing a state where a flat-plate lamination-type conductive polymer actuator is assembled by further adding another link member to the flat-plate lamination-type conductive polymer actuator of FIG. 15C, thereby serving as a modified example of the fifth embodiment.
Figure 15F:
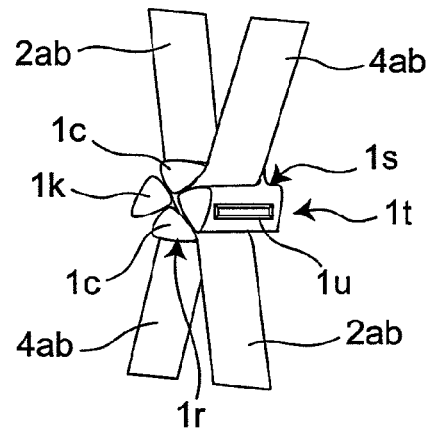
FIG. 15F is an explanatory view showing the flat-plate lamination-type conductive polymer actuator of FIG. 15E in accordance with the modified example of the fifth embodiment being assembled.
Figure 15G:
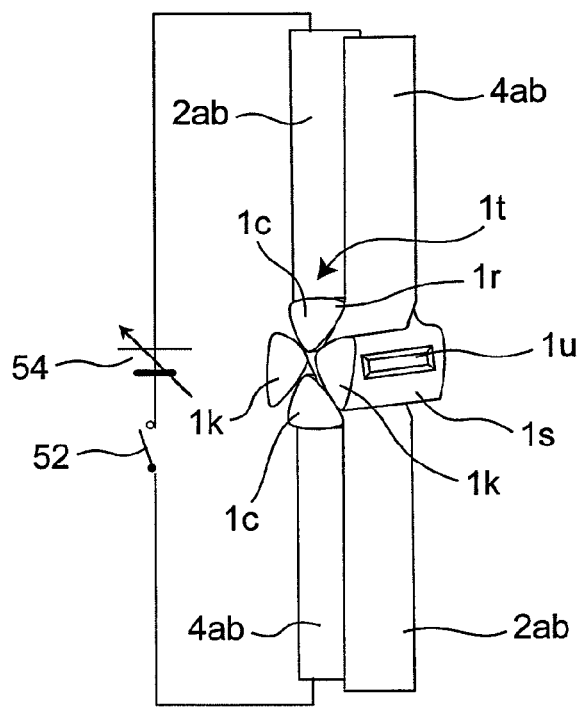
FIG. 15G is an explanatory view of a state where wiring is further attached to the flat-plate lamination-type conductive polymer actuator of FIG. 15F.
Figure 15H:
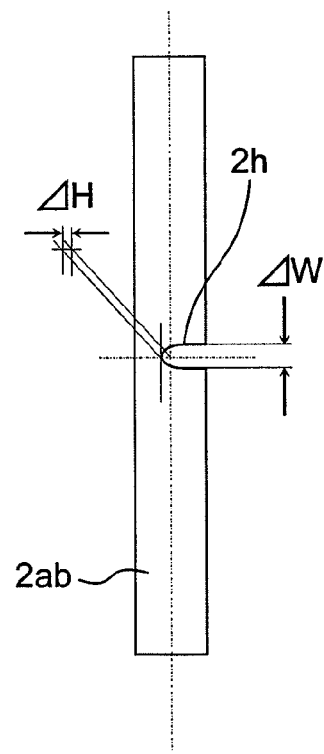
FIG. 15H is a view of one sheet of conductive polymer film used for explaining the structure of the flat-plate lamination-type conductive polymer actuator of FIG. 15F.
Figure 15I:
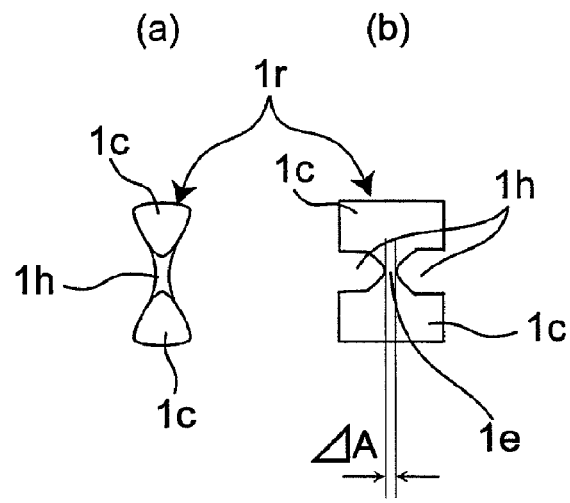
FIGS. 15I(a) and 15I (b) are explanatory views of a fourth link member, being used for explaining the structure of the flat-plate lamination-type conductive polymer actuator of FIG. 15F, while FIG. 15I(a) being a front view thereof and FIG. 15I(b) being a side view thereof.
Figure 15J:
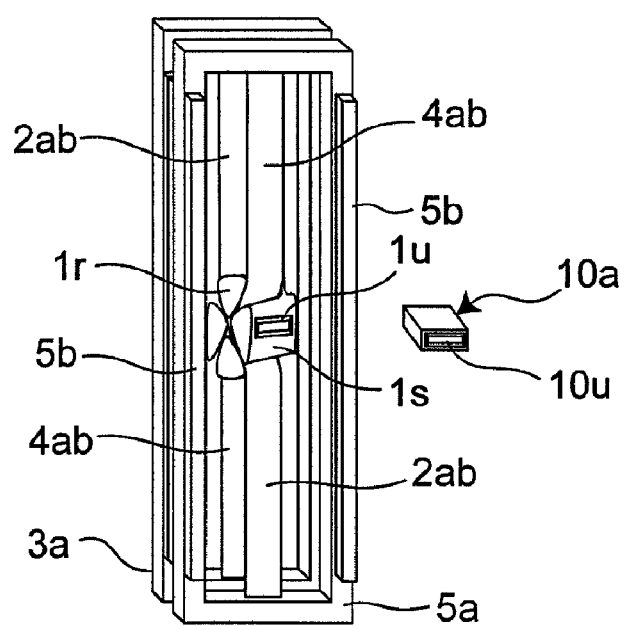
FIG. 15J is an explanatory view showing a state where the flat-plate lamination-type conductive polymer actuator of FIG. 15F is disposed on a fixed frame and is assembled thereon.
Figure 15K:
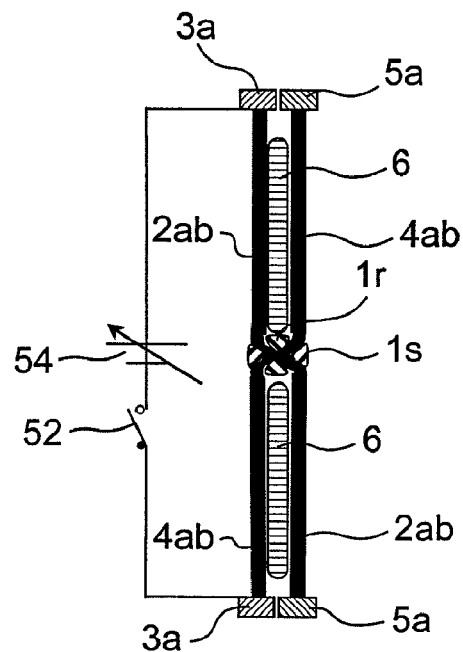
FIG. 15K is a wiring diagram showing one example of the flat-plate lamination-type conductive polymer actuator in accordance with the modified example of the fifth embodiment of the present invention, and applying a voltage to the flat-plate lamination-type conductive polymer actuator.
Figure 15L:
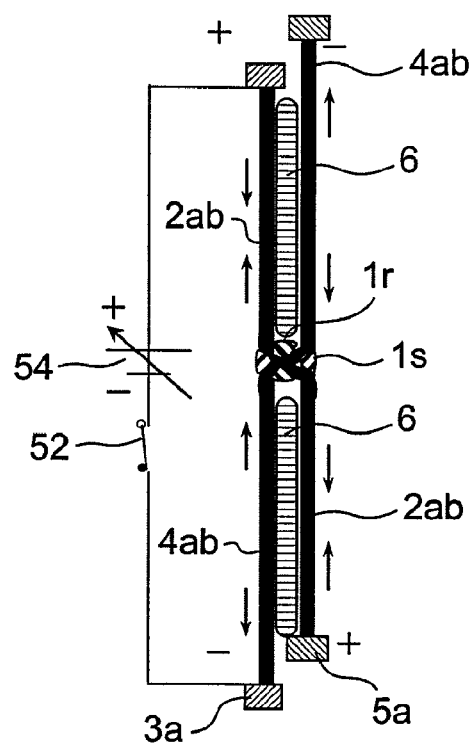
FIG. 15L is a view showing a voltage and a direction of displacement upon turning a switch 52 on in the flat-plate lamination-type conductive polymer actuator of FIG. 15K.
Figure 15M:
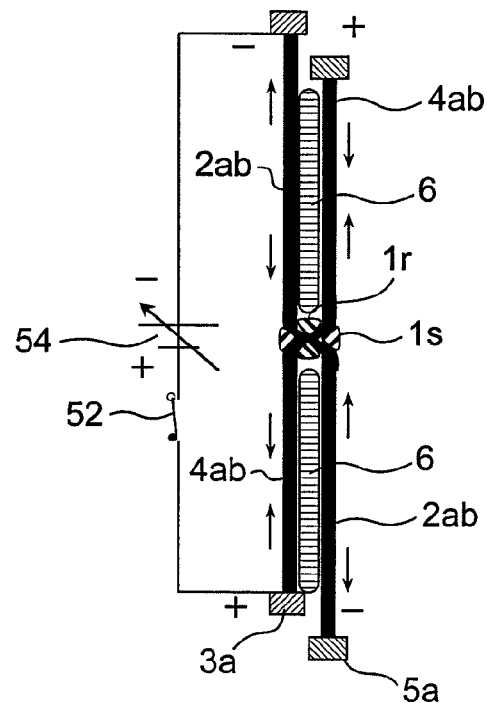
FIG. 15M is a view of a state where a voltage is applied in a direction reversed relative to the voltage applied direction of FIG. 15L to the flat-plate lamination-type conductive polymer actuator of FIG. 15K.
Figure 15N:
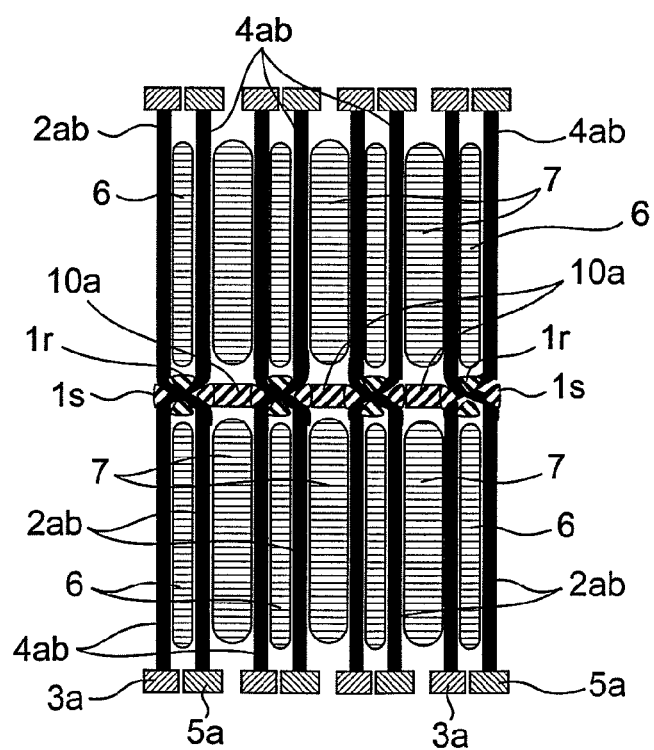
FIG. 15N is a cross-sectional view of a zero-potential state (initial state) showing one example of an actuator device configured by a large number of flat-plate lamination-type conductive polymer actuators in the modified example of the fifth embodiment of the present invention.
Figure 16A:
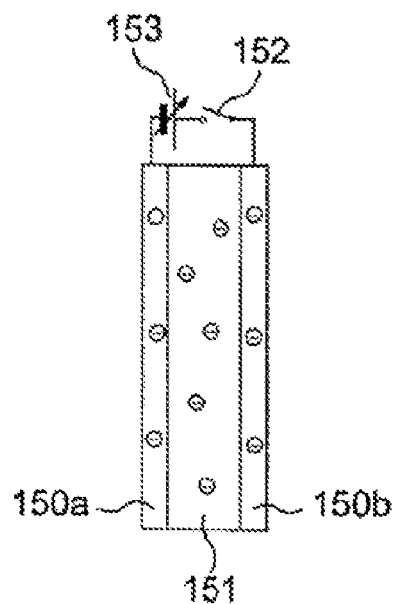
FIG. 16A is a schematic cross-sectional view showing one example of a conventional actuator that utilizes bimorph-type deformation.
Figure 16B:
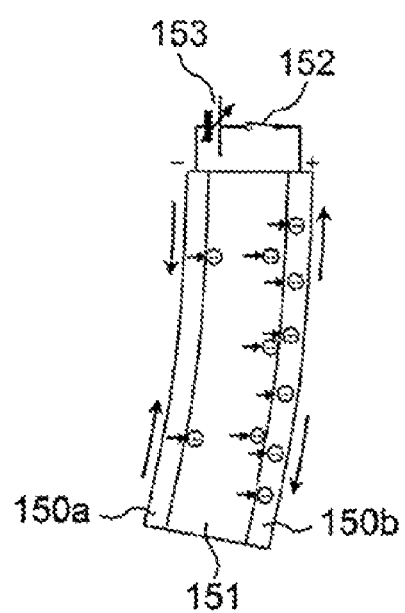
Figure 16C:
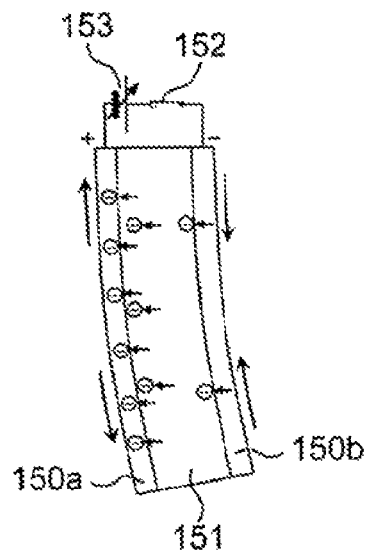
FIG. 16C is a schematic cross-sectional view showing the conventional actuator that utilizes bimorph-type deformation of FIG. 16A in a case where a potential difference thereof is reversed relative to that of FIG. 16B.
Figure 17A:
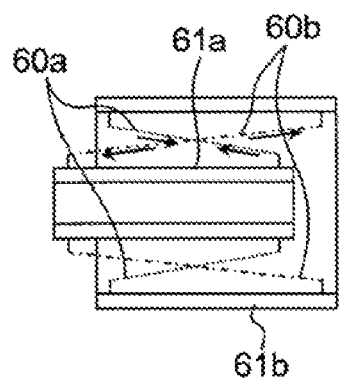
FIG. 17A is a schematic cross-sectional view showing a conventional actuator having a conductive polymer film being formed into a cylindrical shape.
Figure 17B:
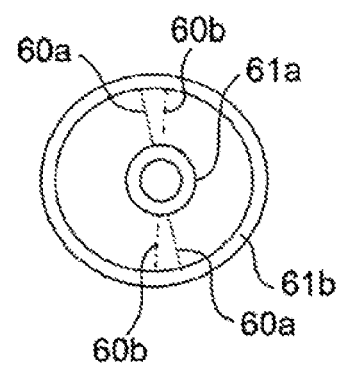
FIG. 17B is a view showing one example of the layout of the conductive polymer film in a circumferential direction in the conventional actuator of FIG. 17A.
Figure 17C:
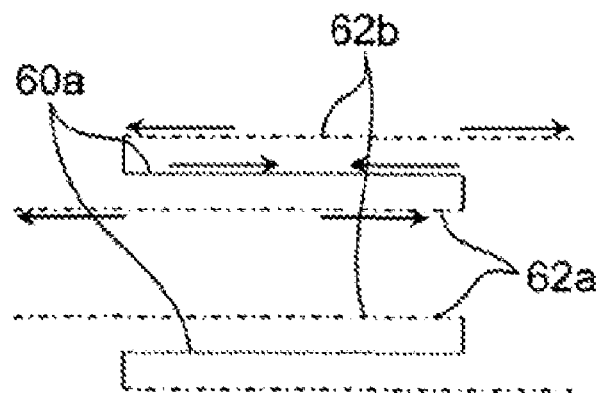
FIG. 17C is a view showing a method for increasing the amount of displacement by forming the cylindrical member with use of a conductive polymer film in the conventional actuator of FIG. 17A.
Figure 18:
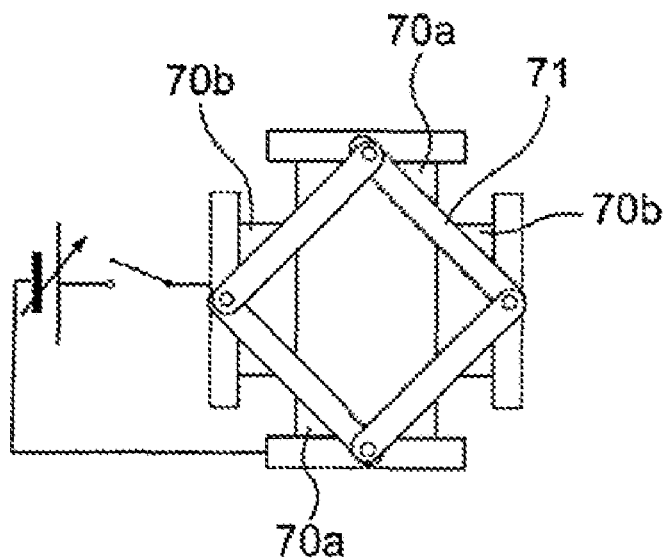
FIG. 18 is a view showing another conventional actuator.

FIGS. 15A to 15N show flat-plate lamination-type conductive polymer actuators in accordance with a fifth embodiment of the present invention and modified examples thereof. In FIGS. 15A to 15N, a seventh conductive polymer film 2ab has a structure in which the first conductive polymer film 2a and the fourth conductive polymer film 4a, as shown in FIGS. 2, 3 and the like, are formed as a sheet of conductive polymer film. That is, an elongated sheet of conductive polymer film having substantially the same length as the coupled length of the first conductive polymer film 2a and the fourth conductive polymer film 4a is prepared as the seventh conductive polymer film 2ab, and one of the sides of the elongated sheet of conductive polymer film (seventh conductive polymer film 2ab) from the center portion is allowed to function as the first conductive polymer film 2a and the other side is allowed to function as the fourth conductive polymer film 4a. An eighth conductive polymer film 4ab has a structure in which the second conductive polymer film 2b and the third conductive polymer film 4b are formed as a sheet of conductive polymer film. That is, another elongated sheet of conductive polymer film having substantially the same length as the coupled length of the second conductive polymer film 2b and the third conductive polymer film 4b is prepared as the eighth conductive polymer film 4ab, and one of the sides of the other elongated sheet of conductive polymer film (eighth conductive polymer film 4ab) from the center portion is allowed to function as the second conductive polymer film 2b and the other side is allowed to function as the third conductive polymer film 4b. As shown in FIG. 15A, the seventh conductive polymer film 2ab and the eighth conductive polymer film 4ab respectively have cut-out portions 2h and 4h in the center portions, each formed by notching one of the side edges in the width direction.

F fourth insulating link member 1r, which has a shape in which two structural members 1c, each having a prism shape, are coupled with each other in the center portions, is designed to have a substantially H-letter shape, with a pair of cut-out portions 1h that face each other between the prism-shaped structural members 1c being formed in the center portion.

In the fourth link member 1r, the cut-out portion 2h of the seventh conductive polymer film 2ab is inserted into one of the cut-out portions 1h (such as the cut-out portion 1h on the left side of FIG. 15A) and combined therewith (see FIG. 15B), with the cut-out portion 4h of the eighth conductive polymer film 4ab being inserted into the other cut-out portion 1h (such as the cut-out portion 1h on the right side of FIG. 15A) and combined therewith (see FIG. 15C), and the seventh conductive polymer film 2ab and the eighth conductive polymer film 4ab are maintained in a manner so as not to be made in contact with each other (see FIG. 15D) so that a power-supply circuit 54 having a built-in voltage-control circuit has its one of electrodes connected to the seventh conductive polymer film 2ab and the other electrode connected to the eighth conductive polymer film 4ab, through a switch 52. The insulating prism-shaped structural member 1c makes it possible to positively prevent the seventh conductive polymer film 2ab and the eighth conductive polymer film 4ab from being made in contact with each other at upper and lower portions of FIG. 15D where they come close to each other.

In a separate manner from this structure, as shown in FIGS. 15E and 15F, a fifth link member (fixed link member) is may be further combined with the fourth link member 1r so that two link members may be prepared as sixth link members it relating to a modified example of the fifth embodiment. In this case, the fifth insulating link member is formed into a substantially U-letter shape, with two prism-shaped structural members 1k having respectively different lengths, being coupled to each other at one of the ends, with a cut-out portion ij being formed from the other end. This cut-out portion ij of the fifth link member is inserted into a portion where the seventh conductive polymer film 2ab and the eighth conductive polymer film 4ab might be made in contact with each other in a state as shown in FIG. 15D so that the insulating prism-shaped structural member 1k is allowed to positively prevent the seventh conductive polymer film 2ab and the eighth conductive polymer film 4ab from being made in contact with each other. With this arrangement, with respect to the seventh conductive polymer film 2ab and the eighth conductive polymer film 4ab, it is possible to prevent the seventh conductive polymer film 2ab and the eight conductive polymer film 4ab from being made in contact with each other, at a portion where the seventh conductive polymer film 2ab and the eighth conductive polymer film 4ab intersect with each other by using the two insulating prism-shaped structural members 1c and the two insulating prism-shaped structural members 1k.

In the fifth embodiment, the link member is formed as only one insulating link member 1r (FIGS. 15A to 15D), or as two link members, that is, the fourth insulating link member 1r and fifth link member (fixed link member) 1s (FIGS. 15E and 15F), as a modified example of the fifth embodiment.

Each of the insulating fourth and fifth link members 1r and is a solid-state member, made of Teflon (registered trademark), or a teak material or the like. As described above, the fourth link member 1r and the fifth link member 1s have a shape in which two members 1c and 1k, each formed into a substantially prism shape, are connected to each other in the center portion in the former, and at the end in the latter.

FIGS. 15A to 15D show examples by which an insulating performance is improved between the seventh and eighth polymer films 2ab and 4ab having mutually different polarities in applied voltages and a wiring system is simplified by integrally forming the conductive polymer films 2a, 2b and 4a, 4b having mutually the same polarity in the applied voltages.

In the seventh and eighth conductive polymer films 2ab and 4ab, cut-out portions 2h and 4h are respectively formed at an intersecting portion between the seventh conductive polymer film 2ab and the eighth conductive polymer film 4ab so as to avoid an electric short circuit. In FIG. 15A, portions indicated by solid lines as cut-outs correspond to these cut-out shapes.

As indicated by the illustration in the center of FIG. 15B, in a case where the seventh and eighth conductive polymer films 2ab and 4ab are connected with each other so as to intersect with each other through the fourth link member 1r, the seventh and eighth conductive polymer films 2ab and 4ab are combined with each other by utilizing the two cut-out portions (concave portions) 1h of the fourth insulating link member 1r. In this case, the fourth insulating link member 1r is designed so that the portions where the seventh conductive polymer film 2ab and the eighth conductive polymer film 4ab are made in contact with each other (that is, for example, portions at which the seventh conductive polymer film 2ab and the eighth conductive polymer film 4ab intersect with each other and each portion located at an edge of the portion where the fourth insulating link member 1r, the seventh conductive polymer film 2ab and the eighth conductive polymer film 4ab are respectively made in contact with one another, with the respective curves of the seventh conductive polymer film 2ab and the eighth conductive polymer film 4ab being shifted to linear shapes) are formed into a curved shape. That is, all the corner portions of each structural member 1c having a prism shape are made to have curved smooth shapes so that it is possible to avoid a concentrated stress to the curved portions of the seventh conductive polymer film 2ab and the eighth conductive polymer film 4ab due to a stress exerted upon expansion or contraction of the seventh conductive polymer film 2ab and the eighth conductive polymer film 4ab, and consequently to avoid disconnection or the like of the seventh conductive polymer film 2ab and the eighth conductive polymer film 4ab.

Referring to FIG. 15D, the following description will discuss how the wiring can be made easier. In comparison with the aforementioned structure shown in FIG. 3A, the wiring can be prepared simply by connecting the two poles to the two ends of the seventh conductive polymer film 2ab and the eighth conductive polymer film 4ab. Therefore, upon manufacturing the actuator, the number of manufacturing processes can be reduced to a great degree. In FIG. 15D, so as to clarify the wiring diagram, those members such as fixed frames and the like are not shown in the drawing.

In accordance with the modified example of the fifth embodiment, by using the fifth link member 1s, the number of points to which the seventh conductive polymer film 2ab and the eighth conductive polymer film 4ab are secured is increased so that it becomes possible to prevent a positional deviation from occurring between the seventh conductive polymer film 2ab and the eighth conductive polymer film 4ab. In particular, by attaching the fifth link member 1s to the fourth link member 1r so that portions where the seventh conductive polymer film 2ab and the eighth conductive polymer film 4ab intersect with each other might not be separated from each other even when, in particular, the seventh conductive polymer film 2ab and the eighth conductive polymer film 4ab are slackened, the fifth link member is allowed to have a function for pressing (function for securing) the seventh conductive polymer film 2ab and the eighth conductive polymer film 4ab against the fourth link member 1r.

As described above, FIGS. 15E and 15F show a structure in which the fifth link member is provided as a fixing link member in addition to the fourth insulating link member 1r so that the fourth insulating link member 1r and the seventh and eighth conductive polymer films 2ab and 4ab are secured from the outside. Originally, in the actuator relating to the fifth embodiment, the seventh and eighth conductive polymer films 2ab and 4ab are maintained in a state where tension is always applied by the fixed frames 3a and 5a shown in FIG. 2A to the first conductive polymer film 2a and the second conductive polymer film 2b that form the seventh conductive polymer film 2ab and the fourth conductive polymer film 4a and the third conductive polymer film 4b that form the eighth conductive polymer film 4ab. However, it is assumed that, upon application of external force or vibration to the actuator, the tension applied to any of the conductive polymer films 2ab and 4ab or all of them might be slackened. Even in such a case, by installing the fifth link member 1a therein, the seventh and eighth conductive polymer films 2ab and 4ab can be positively maintained by the fifth link member 1s so as to prevent the seventh and eighth conductive polymer films 2ab and 4ab from being separated from the fourth insulating link member 1r.

Referring to FIGS. 15H and 15I, the following description will explain the dimensional structures of the seventh and eighth conductive polymer films 2ab and 4ab and the fourth insulating link member 1r. On the assumption that the seventh and eighth conductive polymer films 2ab and 4ab are disposed symmetrically, FIG. 15H illustrates only the seventh conductive polymer film 2ab as a representative example, with respect to the seventh and eighth conductive polymer films 2ab and 4ab. In a case where the seventh and eighth conductive polymer films 2ab and 4ab intersect with each other, it is important to insulate them from each other, that is, to prevent the seventh and eighth conductive polymer films 2ab and 4ab from being made in contact with each other, and for this purpose, the cut-out portions 2h and 4h are respectively required for the seventh and eighth conductive polymer films 2ab and 4ab, and the width of each of the cut-out portions 2h and 4h is formed with a value exceeding the center axis by $\Delta W$ from the center position in the width direction of each of the seventh and eighth conductive polymer films 2ab and 4ab, and the depth thereof is formed with a value exceeding the center axis by $\Delta H$ therefrom. The fourth insulating link member 1r is provided with a neck portion 1e formed as a gap $\Delta A$ at a connecting portion of the two prism-shaped structural members 1c so as to avoid contact between the seventh and eighth conductive polymer films 2ab and 4ab. In the seventh and eighth conductive polymer films 2ab and 4ab, $\Delta W/2$ needs to be set to 200 μm or more by taking into consideration a dimensional error in a normal industrial product. For example, when a prototype device with a $\Delta W/2$ value of 0.5 mm is formed, no problems are raised in the insulating performance. On the other hand, in the fourth insulating link member 1r, the width $\Delta A$ at the neck portion 1e is preferably set to 1 mm or more from the viewpoint of sufficient strength. In the prototype device, the width is set to 1 mm, and no problems such as damages to the seventh and eighth conductive polymer films 2ab and 4ab are raised due to stress caused by expansion and contract of the seventh and eighth conductive polymer films 2ab and 4ab. In the seventh and eighth conductive polymer films 2ab and 4ab, the dimension of $\Delta H$ is determined depending on the value of $\Delta A$, and desirably set to $\Delta H=\Delta A/2+200$ μm. When a prototype device with a $\Delta H$ value of 700 μm is formed, no problems are raised in the insulating performance. Insufficient movements of the seventh and eighth conductive polymer films 2ab and 4ab or insufficient face-to-face alignment thereof hardly occur, and even if these become insufficient, it is expected that only small effects are given to the movements of ions in the electrolyte holding layer. In this case, even in a case where $\Delta H$ is set to 700 μm, if there are positional deviations, each corresponding to 700 μm, in both of the seventh and eighth conductive polymer films 2ab and 4ab, the opposing faces are reduced by a total of 1400 μm. Since the thickness of the electrolyte holding layer is 30 to 50 μm and since the width of the seventh and eighth conductive polymer films 2ab and 4ab is 5 mm, non-opposing faces are calculated to be about 28%. However, actually, it is expected that no influences are given to the movements of the seventh and eighth conductive polymer films 2ab and 4ab because of the following two reasons. That is, the first reason is that, since both of the seventh and eighth conductive polymer films 2ab and 4ab have their two ends secured by the fixed frames, the fixed frames themselves have a structure capable of moving at a position that allows the face-to-face alignment, and it is considered that, upon application of a stress to the conductive polymer films during an operation, the deviation $\Delta H$ in the link member is automatically corrected and restored to the position that allows the face-to-face alignment. The second reason is that, since the electrolyte holding layer is made in contact with the entire faces of the seventh and eighth conductive polymer films 2ab and 4ab, it is expected that, even if there is any remaining portion that has no face-to-face alignment, a voltage is also applied to ions in the corresponding electrolyte holding layer so that ions are allowed to move, making the influences to the movements of the seventh and eighth polymer conductive films 2ab and 4ab very small.

In FIGS. 15A to 15F, although the seventh and eighth conductive polymer films 2ab and 4ab are illustrated as if the two ends thereof were made apart from each other in an X-letter state; however, this illustration is given so as to clarify an assembling or wiring operation, and upon completion by the use of the fixed frames 3a and 5a, the seventh and eighth conductive polymer films 2ab and 4ab are made substantially in parallel with each other, with the electrolyte holding layer 6 being sandwiched therebetween. That is, for example, the resulting structure is shown in FIG. 15G.

FIG. 15J shows a state thereof assembled so as to be set into the fixed frames 3a and 5a, and FIG. 15J also shows the link-member coupling member 10a serving as an insulator. An engaging concave portion 1u is formed in the fifth insulating link member 1s, and engaging convex portions 10u with which the engaging concave portion 1u is engaged are formed on the two ends of the link-member coupling member 10a. Similarly to the case of FIG. 6A, as shown in FIG. 15L that will be described later, between adjacent actuators, the engaging convex portion 10u of one of the ends of the link-member coupling member 10a is engaged with the engaging concave portion 1u of the fifth link member 1s of one of the actuators, while the engaging convex portion 10u of the other end of the link-member coupling member 10a is engaged with the engaging concave portion 1u of the fifth link member 1s of the other actuator. As a result, the adjacent actuators can be coupled and disposed by the link-member coupling member 10a with a predetermined interval therebetween. In this manner, the link-member coupling member 10a has a function for preventing contact between the adjacent conductive polymer films, similarly to the aforementioned link-member coupling member 10.

Technical points devised in this link-member coupling member 10a are recited as follows:

(1) Both of the insulating function and securing function in the seventh and eighth conductive polymer films 2ab and 4ab that originally intersect with one another, and consequently are very difficult to prevent from being made in contact with each other can be achieved by using simple members, such as the fourth link member 1r or the fourth link member 1r and the fifth link member 1s.

(2) The insulating fourth link member 1r and link-member coupling member 10a are formed into shapes that are easily connected to each other.

(3) The cut-out portions 2h and 4h of the seventh and eighth conductive polymer films 2ab and 4ab can be easily formed by using, for example, a press machining process or a laser machining process.

(4) Teflon (registered trademark) or the like can be selected as a material having a corrosion-resistant function against the gel-state ionic liquid that forms the electrolyte holding layers 6 and 7, which is used for the fourth insulating link member 1r.

FIGS. 15K, 15L and 15M show the above-mentioned structures and operations to be carried out in the structures, and are cross-sectional views that are the same as FIGS. 3A, 3B and 3C in the aforementioned embodiment. That is, FIG. 15K is a wiring diagram showing a flat-plate lamination-type conductive polymer actuator relating to a modified example of the fifth embodiment of the present invention and one example of a structure in which a voltage is applied to the conductive polymer actuators. FIG. 15L is a view showing a voltage and a direction of displacement upon turning a switch 52 on in the conductive polymer actuator of FIG. 15K. FIG. 15M is a view showing a state where a voltage is applied to the conductive polymer actuator of FIG. 15K in a direction reversed relative to the voltage applying direction of FIG. 15L. The power supply circuit 54 having a built-in voltage-control circuit has its one of electrodes connected to the conductive polymer film 2ab and the other electrode connected to the conductive polymer film 4ab, respectively, through the switch 52.

As described above, the present fifth embodiment is characterized in that the insulating performance is improved between the conductive polymer films 2ab and 4ab having different polarities in the applied voltages, in that the wiring can be simplified by integrally forming the conductive polymer films whose polarities of the applied voltages are the same, and in that, by avoiding a stress concentration in a bent portion upon connection between the link members 1r and 1s, problems such as disconnection or the like between the seventh conductive polymer film 2ab and the eighth conductive polymer film 4ab can be avoided.

The prism-shaped structural member 1c of the fourth link member 1r and the prism-shaped structural member 1k of the fifth link member 1s are respectively formed into prism shapes respectively; however, not limited to this shape, any desired shape may be used as long as the same insulating function can be obtained.

(Applied Examples)

The flat-plate lamination-type conductive polymer actuator (actuator device) of the present invention may be applied to an actuator for a robot hand 100.

Figure 12A:
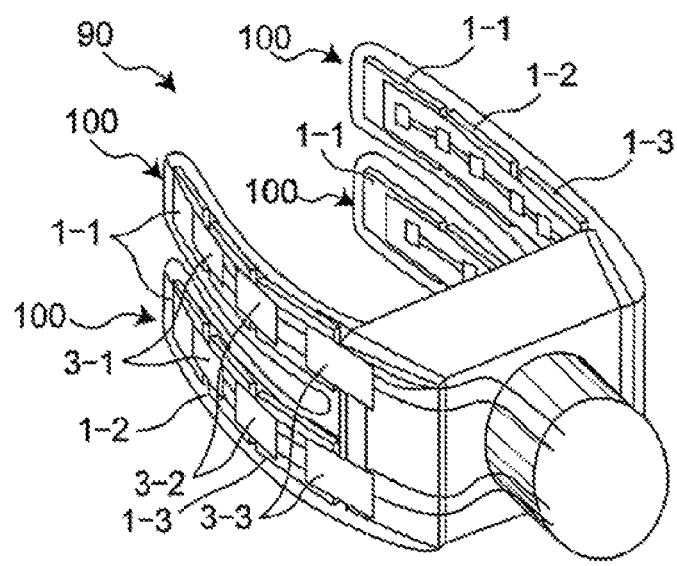
FIG. 12A is a perspective view showing a state where one example of the flat-plate lamination-type conductive polymer actuator device in accordance with the above embodiment of the present invention is applied to a four-finger type holding hand.

FIG. 12A is a perspective view showing a robot hand 90 quoted from FIG. 3A in Japanese Patent No. 3723818. Actuators 3-1, 3-2 and 3-3, serving as driving sources, are described, and as the parts for these actuators 3-1, 3-2 and 3-3, the aforementioned structures, as shown in FIGS. 6A to 6D, in particular, the combination as shown in FIG. 6D, can be used as one example of the flat-plate lamination-type conductive polymer actuator (actuator device) of the present invention so that a large stress, which has been difficult to achieve by using a single film of the conductive polymer film, can be achieved in a space-saved state.

Figure 12B:
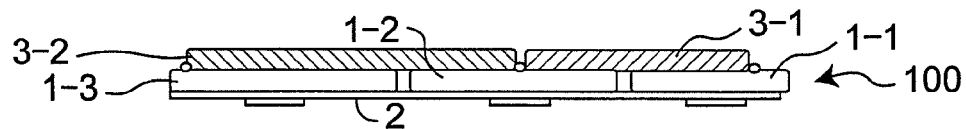
FIG. 12B is a side view partially including a cross section of a joint driving mechanism of the four-finger holding hand of FIG. 12A.
Figure 12C:
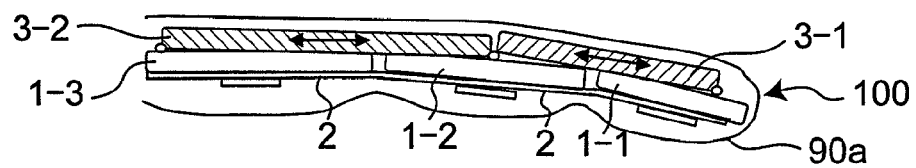
FIG. 12C is a side view partially including a cross section of a modified state of the joint driving mechanism of the four-finger holding hand of FIG. 12A.

More specifically, as indicated by a flat-face-type multi-joint driving mechanism shown in FIGS. 12B and 12C, the actuators 3-1 and 3-3 (the flat-plate lamination-type conductive polymer actuator (actuator device) of the present invention) are expanded and contracted so that a finger 100 of a robot hand 90 can be bent and extended. In this structure, an increase in the stress or the amount of displacement is required for the flat-plate lamination-type conductive polymer actuators 3-1 and 3-2, as will be described later. In this case, a plurality of skeleton members 1, for example, three skeleton members 1-1, 1-2 and 1-3, each having a rectangular plate-shape, and one elongated coupling member 2 having a rectangular plate shape are provided, and the finger 100 is bent by using the torque in the thickness direction.

Figure 12D:
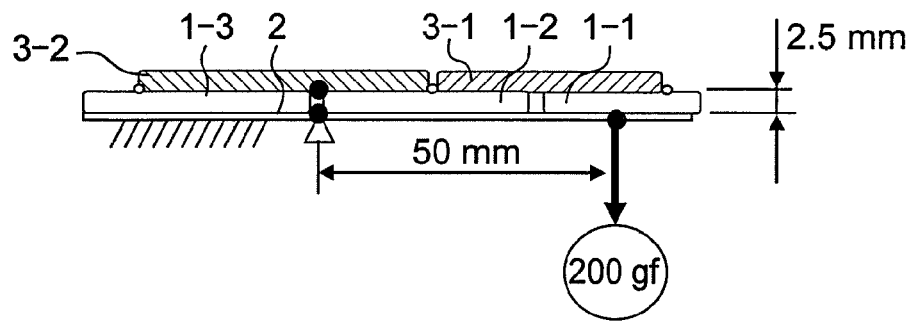
FIG. 12D is a side view partially including a cross section illustrating an actual dimensional example of the joint driving mechanism of the four-finger holding hand of FIG. 12A.

More specifically, FIG. 12D shows the flat-plate lamination-type multi-joint driving mechanism of FIGS. 12B and 12C that is formed as a model with actual sizes written therein. In the model of FIG. 12D, the following description will discuss one example of actual designed numeric values. Suppose that an object serving as a light weight object having 1 kgf is grabbed by this robot hand 90. At this time, it is assumed that, although it also depends on the material of the surface (cover) 90a of the fingers 100 of the robot hand 90, a grabbing force to be required is about 200 gf. As a result, the distance between the load exerted on the tip portion of the finger 100 and the fulcrum of the finger 100 is 50 mm, while the distance between the fulcrums in the thickness direction of the finger 100 is 2.5 mm. Consequently, the displacement enlarging rate in the flat-face-type multi-joint driving mechanism is regarded as (50 mm/2.5 mm)=20 times. Therefore, since the stress becomes 1/20, the actuator 3-2 is required to exert a stress of 4 kgf so as to output the grabbing force of 200 gf. In contrast, supposing that the required amount of displacement for grabbing corresponds to about 10 mm per each joint, the amount of displacement of the actuator 3-2 is set to only 0.5 mm that is 1/20.

For example, a structure shown in FIG. 6D may be used as the flat-plate lamination-type conductive polymer actuator. In this case, in order to obtain the stress and amount of displacement required for a grabbing operation, by using three pieces of the flat-plate lamination-type polymer actuators of FIG. 2D are used as shown in FIG. 6D so that a structure as shown in FIG. 4A (although four pieces of the flat-plate lamination-type conductive polymer actuators of FIG. 2D are used in FIG. 4A, only one of the flat-plate lamination-type polymer actuators of FIG. 2D is removed from this drawing), and three sets of the structure of FIG. 4A are used for forming the structure of FIG. 6D so that the amount of displacement is made 6 times as much, with the stress being set to 3 times as much. In contrast, in FIG. 12D, by using five pieces of the flat-plate lamination-type polymer actuators of FIG. 2D are used so that a structure as shown in FIG. 4A (although four pieces of the flat-plate lamination-type conductive polymer actuators of FIG. 2D are used in FIG. 4A, one of the flat-plate lamination-type polymer actuators of FIG. 2D is further added to this drawing) is used, and 100 sets of the structure of FIG. 4A are used for forming the structure of FIG. 6D so that the amount of displacement is set to 0.5 mm that is 10 times as much, with the stress being set to 4 kgr that is 100 times as much. For example, suppose that in a case where the width of the conductive polymer film is mm, about 20 gr is obtained as the stress of the conductive polymer film. Therefore, in this structure of FIG. 12A, when 10 mm, which is twice as long, is used as the width of the conductive polymer film, the stress is set to about 40 gr, while the generated displacement of the conductive polymer film upon application of a voltage is set to about 0.2%; in contrast, in this structure of FIG. 2D, in a case where the length of the conductive polymer film is set to 25 mm, the amount of displacement δ of the conductive polymer film becomes 50 μm; that is, a value of 2δ corresponding to 0.1 mm (=2×50 μm) can be obtained by a set of flat-plate lamination-type conductive high polymer actuators of FIG. 2D as the amount of displacement.

In the above-mentioned example, the schematic dimensions of the flat-plate lamination-type conductive polymer actuator to be used are 10 mm in width, and about 50 mm or more in length; however, the thickness is set to about 10 mm. This shows that, although a finger that is slightly longer in comparison with the size of a finger of the human hand is obtained, the thickness with the same size can be achieved.

In the structure of FIG. 12A, two pairs of fingers 100 are aligned face to face each other so that a structure having a total of four fingers 100 is prepared; however, not limited to this structure, another structure may be proposed in which, like fingers of the human hand, a thumb and four fingers are placed so as to be made substantially face to face with one another, and the thumb requires a stress although displacement thereof is small, while the remaining four fingers, made substantially face to face with the thumb, require a large amount of displacement. In this structure, a flat-plate lamination-type conductive polymer actuator that puts more importance on stress is used as the thumb, while the actuators that have an increased amount of displacement 4 times higher than that of the thumb, with a ¼ of the stress thereof, are used as the other four fingers; thus, a well-balanced structure as a whole may be used as the hand. In this case also, it is not necessarily required to simultaneously operate all the other four fingers that are substantially made face to face with the thumb, and voltages may be applied from the index finger toward the little finger in succession by carrying out a voltage control. Joints may be prepared in each of the fingers, and it is possible to easily achieve such a structure as to give displacement from the base toward the tip in succession.

In a case where there is a margin on the width of a finger such as the thumb and an extremely large stress is required, it is needless to say that, by simply disposing the flat-plate lamination-type conductive polymer actuators in parallel with one another in the width direction of the conductive polymer film, the stress can be increased in proportion to the number of the disposed actuators.

Figure 13A:
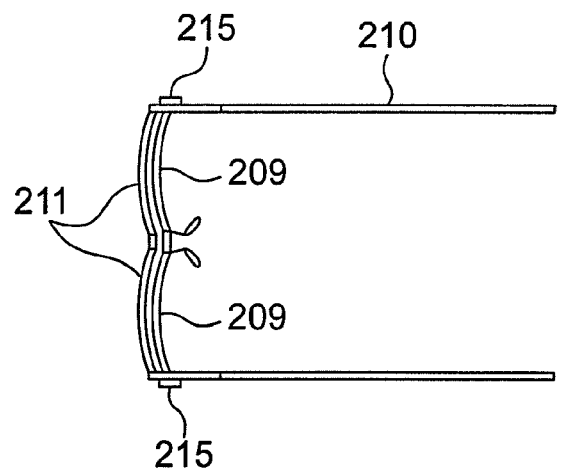
FIG. 13A is a perspective view of a pair of conventional lens-variable glasses.

In addition to the above-mentioned characteristics, since the actuators have characteristics, such as noiseless, light weight and power saving characteristics, they are effectively used as actuators required for wearable apparatuses, and, for example, suitable for use as near and far variable glasses, as shown in FIG. 13A, or a shutter for a digital camera or the like, or a lens-driving mechanism. As shown in FIG. 13A quoted from FIG. 9 in Japanese Unexamined Patent Publication No. 6-3630, the invention of this Patent Document has disclosed so-called near and far focus variable glasses, for use as near and far reading glasses. This structure is based on the premise that the movements of a movable lens 209 for executing a focus variable operation on a glasses frame 210 and a fixed lens 211 are manually carried out (by operating a knob 215 to slide by the hand).

Figure 13B:
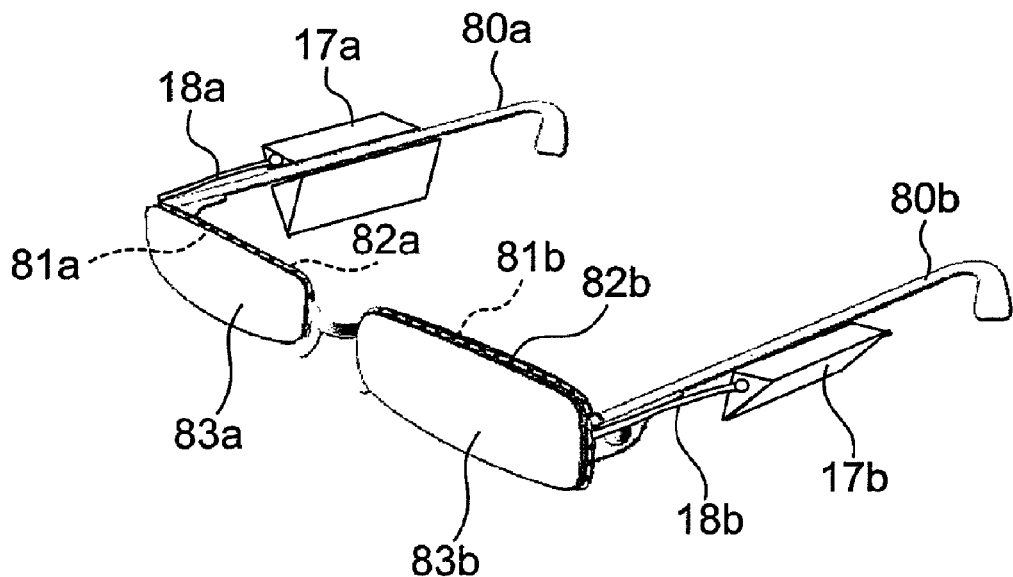
FIG. 13B is a perspective view showing a case where one example of the flat-plate lamination-type conductive polymer actuator device in accordance with the above embodiment of the present invention is applied to the pair of glasses.

In contrast, in the present invention, the flat-plate lamination-type conductive polymer actuator (actuator device) of the present invention can be used to move the lens. For example, as shown in FIG. 13B, the flat-plate lamination-type conductive polymer actuator (actuator device) and the control circuit thereof, a small-size battery and a touch switch are installed in each of controllers 17a and 17b attached to glasses frame portions (temple) 80a and 80b on the right and left sides. Lens driving rods 18a and 18b drawn out of the respective controllers 17a and 17b have their base portions connected to the flat-plate lamination-type conductive polymer actuator (actuator device) and also have their tip portions connected to movable lenses 81a and 81b (such as corresponding to the movable lens 209 in FIG. 13A) respectively supported on rims 82a and 82b on the right and left sides of the glasses frame. Fixed lenses 83a and 83b (such as corresponding to the fixed lens 211 in FIG. 13A) are secured to the rims 82a and 82b on the right and left sides of the glasses frame. The movable lenses 81a and 81b are respectively supported so as to be movable along the optical axis direction relative to the rims 82a and 82b and the fixed lenses 83a and 83b on the right and left sides of the glasses frame (by such a slidable structure as shown in FIG. 13A). With this structure, upon respectively turning on the touch switches of the right and left controllers 17a and 17b, an electric potential is applied to the flat-plate lamination-type conductive polymer actuator (actuator device) by the small-size battery through the control circuit so that the lens driving rods 18a and 18b are allowed to protrude or retreat, thereby making it possible to respectively move the lenses 81a and 81b smoothly to predetermined focal points, and consequently to achieve near and far automatically focusing glasses. In this case also, it is possible to exert large amounts of displacement in both of directions, that is, in the contracting direction and the expanding direction, which has been difficult to achieve by using a single film of the conductive polymer film, and consequently to achieve an actuator (actuator device) having sufficient rigidity and driving force. With respect to this member, by using, in particular, the aforementioned structure as shown in FIGS. 4A to 4C, as the flat-plate lamination-type conductive polymer actuator (actuator device) of the present invention, it becomes possible to provide a large amount of displacement, which has been difficult to achieve by using a single film of the conductive polymer film, in a space-saved state.

The following description will discuss a principle of the near and far variable focusing operation in which a combination of a concave lens and a convex lens are used. In general, a composite focal distance F derived from a combination of lenses having focal distances $f_1$ and $f_2$ is found based upon the following formula by using a distance $\Delta$ between the lenses. $1/F=1/f_1+1/f_2+\Delta/(f_1 \cdot f_2)$. Therefore, the composite focal distance F of a convex lens (+f) and a concave lens (−f) having the same focal distance f is found from the following formula. $1/F=1/f_1-1/f+\Delta/(f_1 \cdot f_2)$. That is, $F=f_2/\Delta$ holds. In a case where the convex lens and the concave lens are overlapped with each other, that is, $\Delta=0$, the composite focal distance F becomes infinite to form a state of the unaided eye. By gradually making the distance $\Delta$ between the lenses greater continuously, the lenses are allowed to function as zooming lenses so that by controlling the distance $\Delta$, it becomes possible to obtain a required setting of zooming. The above-mentioned formulas indicate that, by using a combination of only concave and convex lenses having large focal distances, a large variable focal point F can be obtained by using a small distance $\Delta$. In particular, it is effective that the variable focal point F is represented by a linear function of the distance $\Delta$ between the lenses, and in this case, since the variable focusing process is linearly carried out, the controlling process can be simplified.

Figure 13C:
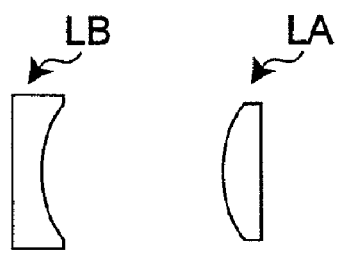
FIG. 13C is a side view including a concave lens and a convex lens that are applicable to the pair of glasses in the flat-plate lamination-type conductive polymer actuator device in accordance with the above embodiment of the present invention shown in FIG. 13B.

More specifically, FIG. 13C has proposed one example of lens specifications that are available as commercial products. A convex lens LA and a concave lens LB, each having a flat surface on one of the faces, which are designed to have the same focal distance, 50 mm, and the outer diameter and the curvature radius that are respectively set to the same value, are selected. As a result, when the face having the curvature of the convex lens LA (curved face on the left side of FIG. 13C) is superposed on the face having the curvature of concave lens LB (curved face on the right side of FIG. 13C), the outer two faces of the convex lens LA and the concave lens LA are formed into a flat-face glass cylindrical shape so that no diffraction strain occurs and the same state as that of the unaided eye can be obtained. However, since the thicknesses of the concave lens LB and the convex lens LA are respectively 6.66 mm and 2.34 mm, the thickness of the cylinder shape at this time becomes 9 mm. In this case, in an attempt to produce a device with its composite focal distance F being variable up to about 2 degree in the magnification as reading glasses, the distance $\Delta$ between the concave lens LB and the convex lens LAs is set to 5 mm from the above-mentioned formula. The degree in the magnification is given as an inverse to the focal distance. As a result, in a case where the concave lens LB and the convex lens LA of FIG. 13C are used, the amount of displacement of each of the lens driving rods 18a and 18b drawn from the controller 17a or 17b in FIG. 13B needs to be 5 mm. The stress required for holding the concave lens LB and convex lens LA is set to about 15 gr for two lenses in a case of glass lenses. In a case where a plastic lens or a Fresnel lens is used, the required stress may be set to 15 gr or less.

Different from the aforementioned robot hand, the designing process of the flat-plate lamination-type conductive polymer actuator is carried out by processes in which, a conductive polymer film having a width of 5 mm is used as the flat-plate lamination-type conductive polymer actuator of FIG. 2D, is used so that, since 20 gr is obtained as a stress, a sufficient stress is prepared against the weight of the lenses. In a case where the length of the conductive polymer film is 25 mm in the structure of FIG. 2D, the amount of displacement $\delta$ of the conductive polymer film becomes about 50 μm; that is, in a case of a pair of flat-plate lamination-type conductive actuators, shown in FIG. 2D, corresponding to about 50 mm in the length in the longitudinal direction of each of the fixed frames 3a and 5a, the amount of displacement is set to 2$\delta$, that is, 0.1 mm (=2×50 μm). Therefore, since, in an attempt to achieve near and far automatically focusing glasses that are variable up to 2 degree in the magnification, 5 mm is required as the amount of displacement as described earlier so that 50 sets of the flat-plate lamination-type polymer actuators of FIG. 2D are required to form the combination as shown in FIG. 4A. Therefore, the thickness of the laminating direction is set to about 5 mm. The weight of only the flat-plate lamination-type conductive polymer actuator is set to about 2 gr or less so that, even when the other control circuit, the small-size battery and the touch switch are included, the resulting structure has a size and a weight that are not so bulky, even if it is attached to the lens frame portion (temple). If necessary, the devices including the small-size battery, or the control circuit or the like may be separated from the glasses frame portion (temple), and may be formed into a portable size so as to be put into a chest pocket or the like.

In particular, in comparison with a piezoelectric element or a stepping motor serving as a conventional small-size actuator, the flat-plate lamination-type conductive polymer actuator of the present invention is also characterized in that a noiseless system can be achieved. In a case of an electric appliance to be used at a position that is most sensitive in auditory sensation or tactual sensation, such as a glasses frame, a noiseless characteristic provides an important advantage.

In the embodiment of FIG. 13B, controlling operations are carried out on the right and left lenses individually; such operations are carried out based upon the fact that, in most cases, actual needs of reading glasses call for different degrees of magnification between the right and left lenses.

In the above description, in an attempt to variably change the degree of magnification from zero to 2, the amount of displacement is set to 5 mm, and since the variable focusing operation is linearly carried out relative to the distance $\Delta$ between the lenses, this system is also characterized in that, in a case where the degree of magnification is changed only by 1 degree, the amount of displacement only needs to be set to 2.5 mm, which is half the amount of displacement of 5 mm. The amount of displacement of the conductive polymer film is non-linearly changed relative to the voltage so that it has a hysteresis; however, since the amounts of displacement in the lens driving rods 18a and 18b are linearly changed, and this fact makes it possible to simplify the entire controlling operations. As the reading glasses, the necessary limit of the degrees of magnification is up to three to four degrees, and most of users' demands in their mid-forties and fifties are sufficiently covered by three degrees, that is, zero, 1 and 2, in magnification, as near, middle and far applications (long-distance-use, middle-distance-use and short-distance-use) in most cases. Of course, even in a case where 3 or more is required in the degree of magnification, it is possible to deal with such a case by selecting those having a lens with a shorter focal distance, or by increasing the amount of displacement of the lens driving rod 18a or 18b.

Although the structure as shown in Japanese Unexamined Patent Publication No. 6-3630 relates to the manual operation, the present invention makes it possible to carry out electric control; therefore, by attaching a distance sensor to the glasses frame, the distance from an object that the user is viewing can be automatically measured by the distance sensor, and based upon information obtained by the distance sensor, the lens driving rods 18a and 18b can be driven and controlled by the controllers 17a and 17b; thus, it becomes possible to efficiently vary the degree of magnification of the glasses automatically, and consequently to achieve an efficient system. In this case, however, when the speed at which the movable lens is variably shifted is too fast, or in contrast, when the speed at which the movable lens is variably shifted is too slow, the user might feel uncomfortable; therefore, the variable speed to provide an appropriate amount of displacement needs to be controlled properly.

In a case of the robot hand shown in FIG. 12A, a stress in a grabbing direction is required, while not so much stress is particularly required in a reversed direction; however, in a case of the near and far automatic focusing glasses shown in FIG. 13B, stresses are required in two directions of displacement, and for this reason, in particular, the flat-plate lamination-type conductive polymer actuator of the present invention can be effectively applied.

In a case of wearable appliances, since noiseless, light-weight and power-saving characteristics form the most important factors, it has been difficult to use the conventional piezoelectric element or air-pressure actuators; however, from now on, the wearable appliances are best-suited objects to which the actuator (actuator device) of the present invention is applied.

In the future, it is expected that the robot hands or near and far automatic focusing glasses will be widely used as domestic appliances, and in this case, to provide soft appliances is one of important factors. Since the conductive polymer film exerts its own characteristic as an elastic member, one of the important effects is to absorb an impact of a collision between the robot hand and a man or an impact applied to a lens in the near and far automatic focusing glasses. From these points of view also, the present invention is optimally utilized as actuators for home electric appliances.

For example, the link member 1 of FIG. 2A has been explained as a single link member that is integrally formed by the first link member and the second link member by using the same member; however, the first link member and the second link member may be respectively formed not by the same member, but by different members so as to be coupled to each other to form a single member.

Furthermore, the above description has been given based upon the premise that, in accordance with the operation principle of the actuator using conductive polymer disclosed in Patent Document 1, anions are inserted into a conductive polymer film so that the film is expanded and, in contrast, anions are removed therefrom so that the film is contracted; however, depending on the kinds of the conductive polymer film or the kinds of the ionic liquid or the combinations thereof, the same phenomenon can be generated not by anions, but by cations. In this case also, it is possible to obtain the same effects by the present invention.

The arrangement in a molecular structure level can be formed in the same manner. The flat-plate lamination-type conductive polymer film can be easily formed by a process similar to the printing process.

While the present invention has been adequately described on the preferred embodiments thereof with reference to the accompanying drawings, it will be apparent to one skilled in the art that various changes and modifications can be made therein. Such changes or modifications are to be regarded, as far as not departing from the scope of the attached claims of the present invention, as being included therein.

By properly combining the arbitrary embodiments of the aforementioned various embodiments, the effects possessed by the embodiments can be produced.

(Differences between the Present Invention and the Prior-Art Documents)

FIGS. 14A to 14E show structures disclosed in Japanese Unexamined Patent Publication No. 3-243174 and Japanese Unexamined Patent Publication No. 63-289975. FIGS. 14F and 14G are cross-sectional views that show examples in which the structures of the prior-art documents are applied to the flat-plate lamination-type conductive polymer actuator in accordance with the first embodiment of the present invention.

The following description will discuss the structures disclosed in Japanese Unexamined Patent Publication No. 3-243174 and Japanese Unexamined Patent Publication No. 63-289975, and also explain the difference thereof from the present invention and the effects of the present invention.

Figure 14A:
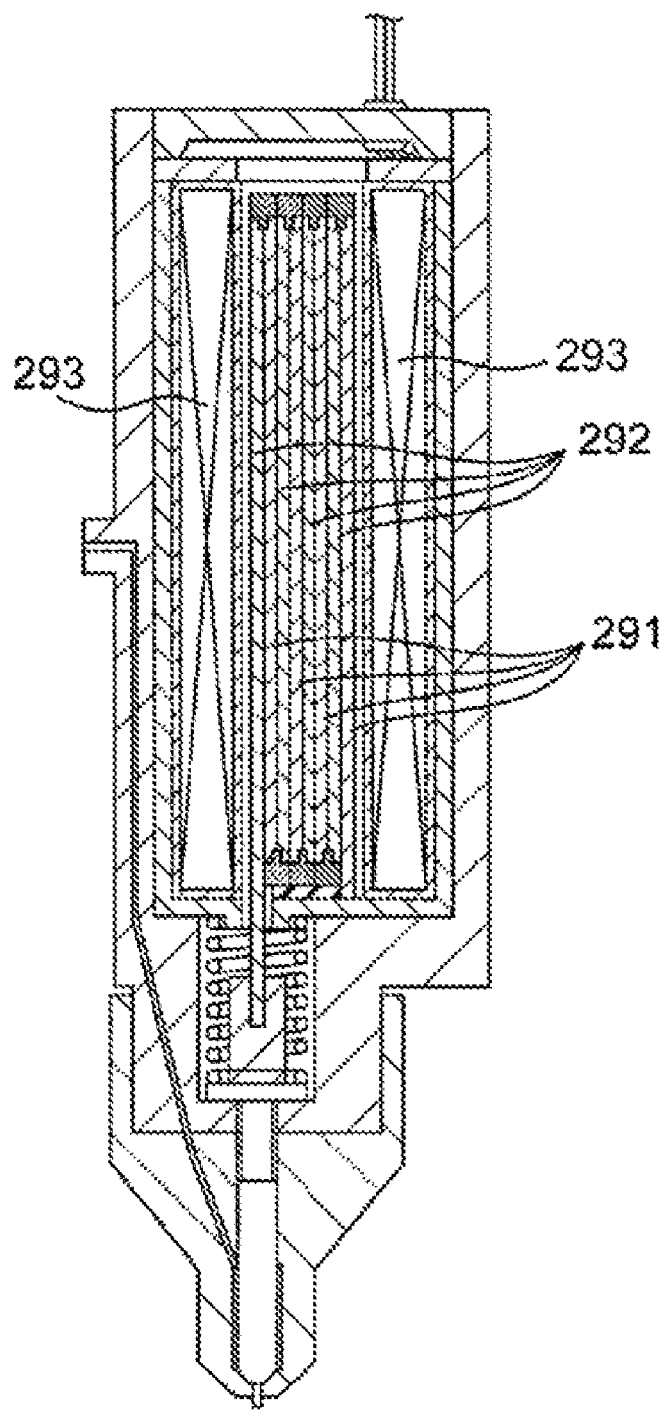
FIG. 14A is a longitudinal cross-sectional view showing a structure disclosed in Japanese Unexamined Patent Publication No. 3-243174.
Figure 14B:
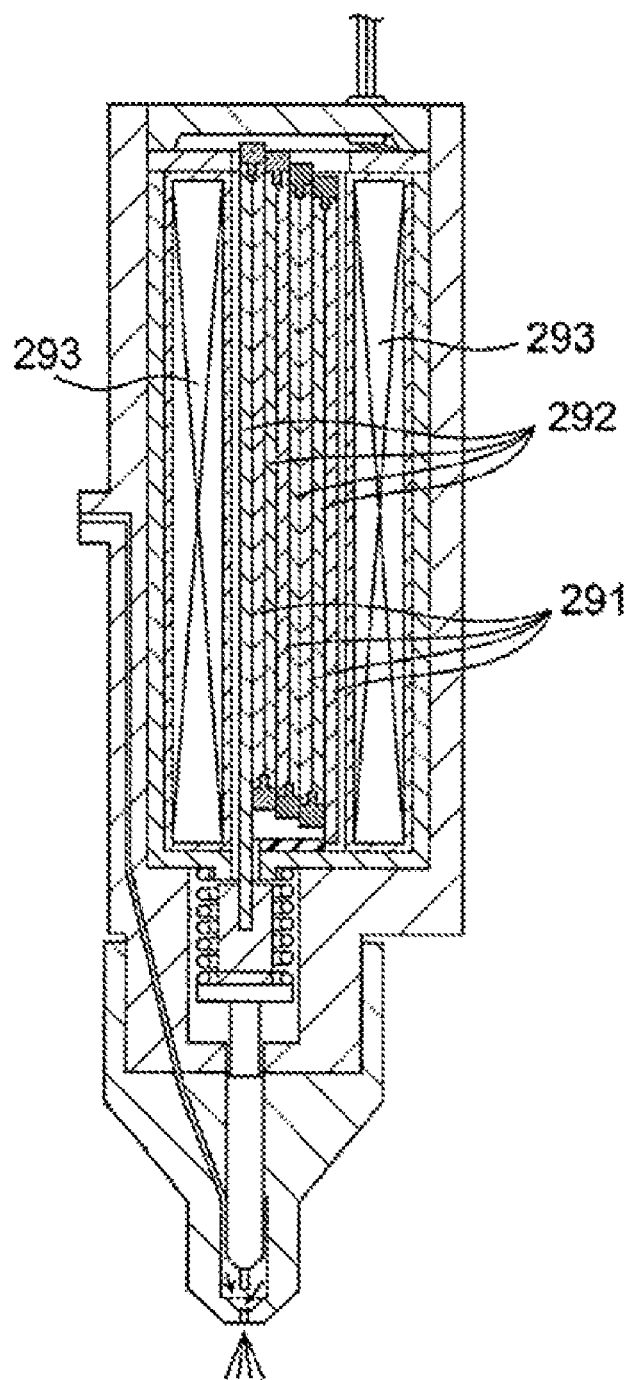
FIG. 14B is a longitudinal cross-sectional view showing the structure disclosed in Japanese Unexamined Patent Publication No. 3-243174 of FIG. 14A.

FIGS. 14A and 14B show structures disclosed by Japanese Unexamined Patent Publication No. 3-243174. In FIGS. 14A and 14B, expansion plates 291 and contraction plates 292 are alternately disposed. Each expansion plate 291 is made of an alloy between rare-earth elements, such as Tb, Dy, Ho, Er and Tm, and a magnetic material, such as Fe and Co, that is, an ultra-magnetostrictive alloy that expands upon generation of a magnetic field, and when power is applied to a solenoid 293, the expansion plate 291 is expanded by the magnetic field generated in the longitudinal direction. Each contraction plate 292 is made of an alloy between Sm that contracts in response to the generation of a magnetic field and Fe or an ultra-magnetostrictive alloy such as Ni or the like, and when power is applied to a solenoid 293, the contraction plate 292 is contracted by the magnetic field generated in the longitudinal direction. The following description will discuss the functions thereof.

When the expansion plate 291 is expanded, and the upper end position of the expansion plate 291 is raised. As it is raised, the contraction plate 292 moved above is contracted. Thus, the lower end position of the contraction plate 292 is raised by an added amount of the amount of expansion of the expansion plate 291 and the amount of contraction of the contraction plate 292. Consequently, the expansion plates 291 and the contraction plates 292 alternately disposed are expanded and contracted so that the entire structure is allowed to rise. In this case, the expansion plate 291 and the contraction plate 292 are respectively prepared as flat-plate-shaped members.

Figure 14C:
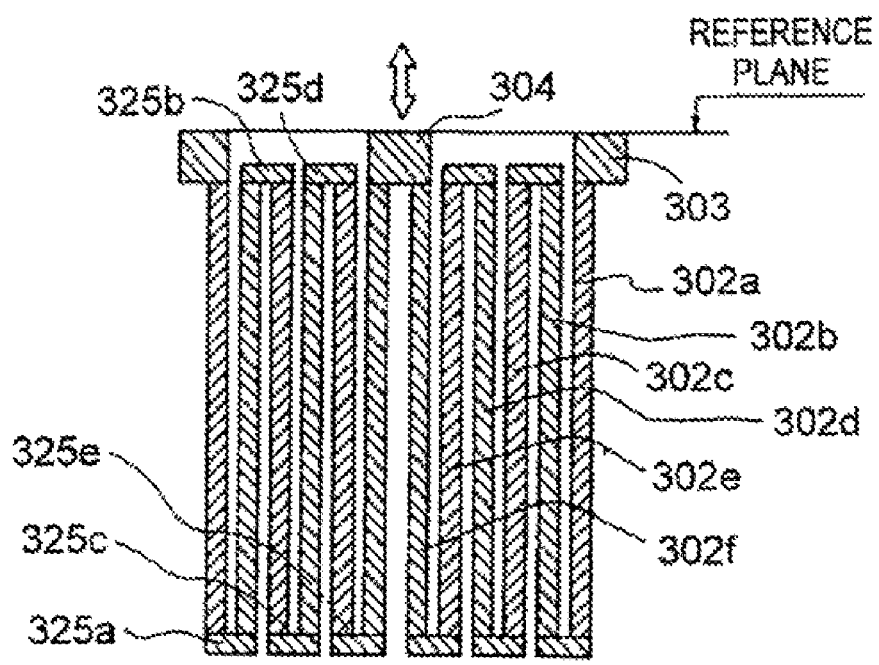
FIG. 14C is a longitudinal cross-sectional view showing a structure disclosed in Japanese Unexamined Patent Publication No. 63-289975.
Figure 14D:
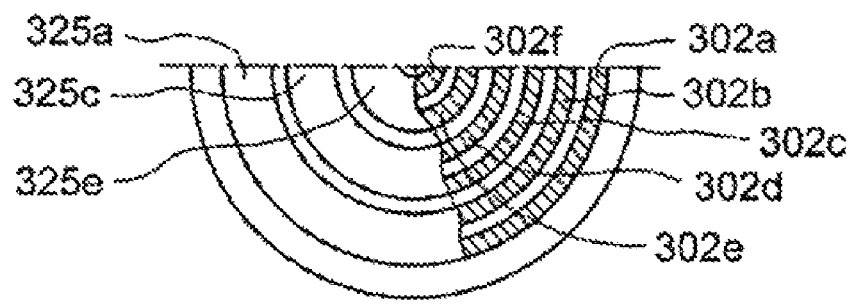
FIG. 14D is a partially exploded lateral cross-sectional view showing the structure disclosed in Japanese Unexamined Patent Publication No. 63-289975 of FIG. 14C.
Figure 14E:
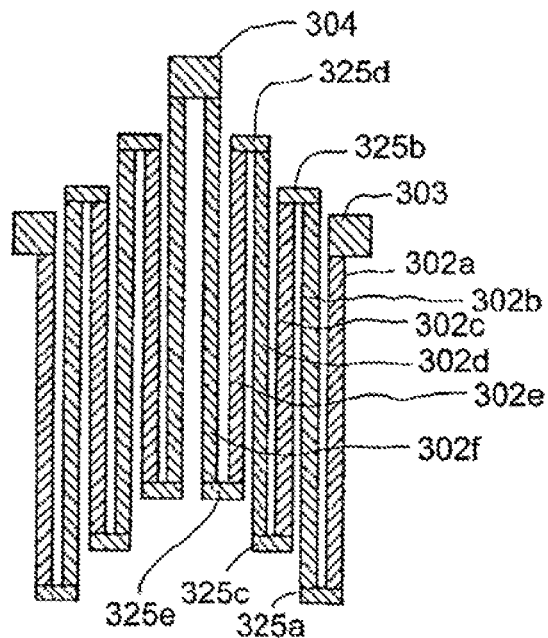
FIG. 14E is a longitudinal cross-sectional view showing the structure disclosed in Japanese Unexamined Patent Publication No. 63-289975 of FIG. 14C.
Figure 14F:
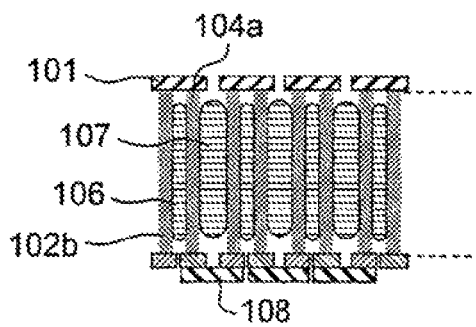
FIG. 14F is a longitudinal cross-sectional view showing an exemplified structure hypothetically considered with respect to a structure and operations relating to the structure easily achieved based on the structures disclosed in Japanese Unexamined Patent Publication No. 3-243174 and Japanese Unexamined Patent Publication No. 63-289975.
Figure 14G:
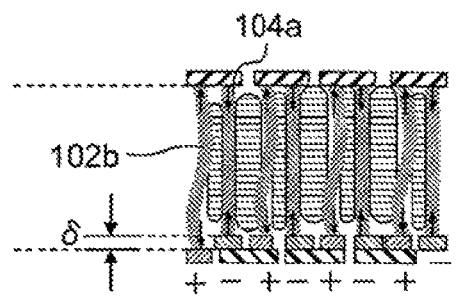
FIG. 14G is a longitudinal cross-sectional view showing operations of the structure of FIG. 14F.

FIGS. 14C to 14E show a structure disclosed in Japanese Unexamined Patent Publication No. 63-289975. Tube-shaped solid-state elements (piezoelectric lamination bodies) 302a, 302b, 302c, 302d, 302e and 302f having different diameters, which are connected to one another by annular joining members 325a, 325b, 325c, 325d, 325e and 325f, can be expanded by accumulating expansion of the respective solid-state elements 302a, 302b, 302c, 302d, 302e and 302f so that an amount of displacement between the housing 303 of a valve and the tube-shaped valve member 304 forms a stress to be externally applied. These solid-state elements 302a, 302b, 302c, 302d, 302e and 302f are characterized in that they have ring shapes in their cross-sectional plan views, as shown in FIG. 14D.

Next, FIGS. 14F and 14G show a structure that is slightly similar to the structure of the present invention shown in FIGS. 4A and 4B, and can be easily arrived based upon the structures disclosed by Japanese Unexamined Patent Publication No. 3-243174 and Japanese Unexamined Patent Publication No. 63-289975, and correspond to drawings in which operations by the structure are hypothetically considered. More specifically, FIGS. 14F and 14G show cross-sectional views of an actuator that is configured by extracting only a portion in one direction from the position where the link member 1 is placed, for example, only the structure on the lower side of FIG. 4A, of the structure of the present invention shown in FIGS. 4A and 4B. In FIGS. 14F and 14G, reference symbol 101 represents a coupling member, reference symbols 102*b* and 104*a* represent conductive polymer films, reference symbols 106 and 107 represent electrolyte holding layers, and 108 represents a coupling member.

The conductive polymer film that is dealt by the present invention is allowed to output a stress in the contracting direction by the tension of the film. However, in general, the conductive polymer film has such a characteristic that it is easily buckled when expanded. FIG. 14G shows such a state. The contracting conductive polymer film 104*a* is allowed to exert a tensile stress; however, in an attempt to utilize a pressing force of the conductive polymer film 102*b* that is trying to expand, the conductive polymer film 102*b* tends to be buckled. Therefore, in the structure shown in FIG. 14F, although the conductive polymer films 104*a* and 102*b* are laminated, no effect for expanding the amount of displacement of the entire actuator is obtained.

In Patent Document Japanese Unexamined Patent Publication No. 63-289975 shown in FIGS. 14C to 14E, since the solid-state elements 302*a*, 302*b*, 302*c*, 302*d*, 302*e* and 302*f* are tube-shaped members, they are comparatively resistant to buckling. In the same manner, even when these are replaced by tube-shaped conductive polymer films, the resulting device is not suitable for practical use, although the effect for suppressing buckling can be expected slightly. More specifically, because of the ring shape, the number of laminated layers is limited by the diameter. In other words, since the actuator becomes bulky in an attempt to suppress buckling, the resulting device is not suitable for practical use. Since the areas of the face-to-face conductive polymer films become different depending on the radial directions, many problems are raised upon controlling.

The inventors of the present invention have found that, in a case where a conductive polymer film is used as an expanding and contracting material, which has not been disclosed by Japanese Unexamined Patent Publication No. 3-243174 and Japanese Unexamined Patent Publication No. 63-289975, a problem arises in that the expanded conductive polymer film is buckled. By using a structure in which the link member and the fixed frame are adopted as shown in the aforementioned first to fifth embodiments of the present invention, the displacement of the actuator utilizing the conductive polymer film can be positively expanded, or the stress can be positively expanded.

The flat-plate lamination-type conductive polymer actuator and flat-plate lamination-type conductive polymer actuator device, as well as the operating method, relating to the present invention, provide rigidity and a driving force bidirectionally, that is, in the contracting direction and the expanding direction, and make it possible to expand displacement or stress thereof by the laminated structure, and by utilizing a structure in which conductive polymer films that contract and expand are made face to face with each other, with an electrolyte holding layer interposed therebetween, it becomes possible to provide an actuator that can carry out an efficient driving operation with energy and space being saved, and the resulting actuator is effectively applied as an artificial muscle actuator, and desirably used for a driving unit for an robot arm or a robot hand of a robot.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A flat-plate lamination-type conductive polymer actuator comprising:

a first link member for holding ends on one side being made face to face with each other of a first conductive polymer film and a second conductive polymer film;

a first fixed frame for holding ends on another side of the first conductive polymer film and the second conductive polymer film;

a second link member for holding ends on one side being made face to face with each other of a third conductive polymer film and a fourth conductive polymer film;

a second fixed frame for holding ends on another side of the third conductive polymer film and the fourth conductive polymer film;

a first electrolyte holding layer disposed between the first conductive polymer film and the third conductive polymer film; and a second electrolyte holding layer disposed between the second conductive polymer film and the fourth conductive polymer film, the first fixed frame and the second fixed frame being placed adjacent to each other, so that the first conductive polymer film and the third conductive polymer film are connected to each other, with the first electrolyte holding layer being interposed therebetween, while the second conductive polymer film and the fourth conductive polymer film are connected to each other, with the second electrolyte holding layer being interposed therebetween, with the first link member being connected to the second link member, wherein by applying an electric potential difference between the first conductive polymer film and the third conductive polymer film, one of the first conductive polymer film and the third conductive polymer film is expanded by a redox reaction, while another thereof is contracted, and by applying an electric potential difference between the second conductive polymer film and the fourth conductive polymer film, one of the second conductive polymer film and the fourth conductive polymer film is contracted by a redox reaction, while another thereof is expanded, and a sum of a contraction displacement in the first fixed frame and a contraction displacement in the second fixed frame is allowed to form a relative displacement between the first fixed frame and the second fixed frame, by connecting the first link member and the second link member.

2. The flat-plate lamination-type conductive polymer actuator according to claim 1, wherein the first link member holds the respective ends of the first and second conductive polymer films and also electrically insulates the respective ends from each other, while the second link member holds the respective ends of the third and fourth conductive polymer films and also electrically insulates the respective ends from each other.

3. The flat-plate lamination-type conductive polymer actuator according to claim 1, wherein the electric potential difference to be applied between the first conductive polymer film and the third conductive polymer film and the electric potential difference to be applied between the second conductive polymer film and the fourth conductive polymer film are applied so as to make the displacement due to expansion and contraction of the first to fourth conductive polymer films caused by the redox reactions equal to one another.

4. The flat-plate lamination-type conductive polymer actuator according to claim 3, wherein the first and second conductive polymer films are made by a same material so as to have a same length, and the third and fourth conductive polymer films are made by a same material so as to have a same length.

5. A flat-plate lamination-type conductive polymer actuator device comprising:
  a plurality of flat-plate lamination-type conductive polymer actuators according to claim 1, the actuators being connected with one another with the electrolyte holding layer being interposed therebetween, wherein
  by applying an electric potential difference between the conductive polymer films, one of the adjacent conductive polymer films is expanded by a redox reaction, with another thereof being contracted thereby.

6. A robot hand comprising: the flat-plate lamination-type conductive polymer actuator device according to claim 5, being disposed therein as a driving source for fingers so as to be capable of bending.

7. A pair of glasses comprising: the flat-plate lamination-type conductive polymer actuator device according to claim 5 used for moving a movable lens relative to a lens frame.

8. A flat-plate lamination-type conductive polymer actuator device comprising:
  a plurality of flat-plate lamination-type conductive polymer actuators according to claim 1, the actuators being connected with one another with the electrolyte holding layer being interposed therebetween, wherein
  by applying an electric potential difference between the conductive polymer films, one of the adjacent conductive polymer films is expanded by a redox reaction, with another thereof being contracted thereby, wherein, upon connecting the plurality of flat-plate lamination-type conductive polymer actuators to one another, the fixed frames are coupled to one another.

9. A flat-plate lamination-type conductive polymer actuator device comprising:
  a plurality of flat-plate lamination-type conductive polymer actuators according to claim 1, the actuators being connected with one another with the electrolyte holding layer being interposed therebetween, wherein
  by applying an electric potential difference between the conductive polymer films, one of the adjacent conductive polymer films is expanded by a redox reaction, with another thereof being contracted thereby, wherein, upon connecting the plurality of flat-plate lamination-type conductive polymer actuators to one another, the link members are coupled to one another.

10. A flat-plate lamination-type conductive polymer actuator device comprising:
  a plurality of flat-plate lamination-type conductive polymer actuators according to claim 1, the actuators being connected with one another with the electrolyte holding layer being interposed therebetween, wherein
  by applying an electric potential difference between the conductive polymer films, one of the adjacent conductive polymer films is expanded by a redox reaction, with another thereof being contracted thereby, wherein, upon connecting at least three flat-plate lamination-type conductive polymer actuators to one another, the conductive polymer films, the conductive polymer films placed on every other fixed frame are linearly coupled to one another so as to be charged.

11. The flat-plate lamination-type conductive polymer actuator according to claim 1, wherein the first and fourth conductive polymer films are made by a sheet of conductive polymer film, the third and second conductive polymer films are made by another sheet of conductive polymer film, and the first link member and the second link member are integrally connected to each other to form a single insulating link member so that the sheet of conductive polymer film and the other sheet of conductive polymer film are held by the insulating link member so as not to be made in contact with each other, so as to intersect with each other in center portions.

12. The flat-plate lamination-type conductive polymer actuator device according to claim 1, wherein the first link member and the second link member are formed by the same members or different members that are coupled to each other.

13. A flat-plate lamination-type conductive polymer actuator device comprising:
  a plurality of flat-plate lamination-type conductive polymer actuators according to claim 1, the actuators being connected with one another with the electrolyte holding layer being interposed therebetween, wherein
  by applying an electric potential difference between the conductive polymer films, one of the adjacent conductive polymer films is expanded by a redox reaction, with another thereof being contracted thereby, wherein, upon connecting the plurality of conductive polymer actuators to one another, a spacer is interposed between the fixed frames of the adjacent conductive polymer actuators.

14. An operating method for a flat-plate lamination-type conductive polymer actuator,
  the conductive polymer actuator comprising:
  a first link member for holding ends on one side being made face to face with each other of a first conductive polymer film and a second conductive polymer film,
  a first fixed frame for holding ends on another side of the first conductive polymer film and the second conductive polymer film,
  a second link member for holding ends on one side being made face to face with each other of a third conductive polymer film and a fourth conductive polymer film,
  a second fixed frame for holding ends on another side of the third conductive polymer film and the fourth conductive polymer film,
  a first electrolyte holding layer disposed between the first conductive polymer film and the third conductive polymer film, and
  a second electrolyte holding layer disposed between the second conductive polymer film and the fourth conductive polymer film;
  the first fixed frame and the second fixed frame being placed adjacent to each other so that the first conductive polymer film and the third conductive polymer film are connected to each other, with the first electrolyte holding layer being interposed therebetween, while the second conductive polymer film and the fourth conductive polymer film are connected to each other, with the second electrolyte holding layer being interposed therebetween, with the first link member being connected to the second link member, the method comprising:

by applying an electric potential difference between the first conductive polymer film and the third conductive polymer film, expanding one of the first conductive polymer film and the third conductive polymer film by a redox reaction, while contracting another thereof; and by applying an electric potential difference between the second conductive polymer film and the fourth conductive polymer film, contracting one of the second conductive polymer film and the fourth conductive polymer film by a redox reaction, while expanding another thereof, wherein a sum of a contraction displacement in the first fixed frame and a contraction displacement in the second fixed frame is allowed to form a relative displacement between the first fixed frame and the second fixed frame, by connecting the first link member and the second link member.

* * * * *